(12) United States Patent
Zhang et al.

(10) Patent No.: US 7,943,159 B1
(45) Date of Patent: May 17, 2011

(54) **FEMALE SEX PHEROMONE OF THE DOGWOOD BORER (DWB), *SYNANTHEDON SCITULA*, AND ATTRACTION INHIBITOR (ANTAGONIST)**

(75) Inventors: Aijun Zhang, Silver Spring, MD (US); Tracy C. Leskey, Shepherdstown, WV (US); Christopher J. Bergh, Winchester, VA (US)

(73) Assignees: The United States of America as represented by the Secretary of Agriculture, Washington, DC (US); Virginia Polytechnic Institute and State University, Winchester, VA (US)

( * ) Notice: Subject to any disclaimer, the term of this patent is extended or adjusted under 35 U.S.C. 154(b) by 308 days.

(21) Appl. No.: 12/327,010

(22) Filed: Dec. 3, 2008

Related U.S. Application Data

(63) Continuation-in-part of application No. 11/372,173, filed on Mar. 9, 2006, now abandoned.

(51) Int. Cl.
  *A01N 25/00* (2006.01)
  *A01N 25/08* (2006.01)
  *A01N 37/00* (2006.01)
  *A01N 37/06* (2006.01)
  *A61K 31/21* (2006.01)
  *A61K 31/215* (2006.01)
  *A61K 31/22* (2006.01)

(52) U.S. Cl. ........ 424/405; 424/409; 424/410; 514/506; 514/529; 514/546

(58) Field of Classification Search ................ None
  See application file for complete search history.

(56) References Cited

OTHER PUBLICATIONS

Bergh et al. (The Canadian Entomologist 2003, 135: 615-635).*
Bergh et al. (J. Econ. Entomol 2004, 97(2): 344-352).*

* cited by examiner

*Primary Examiner* — Ernst V Arnold
(74) *Attorney, Agent, or Firm* — John D. Fado; G. Byron Stover

(57) ABSTRACT

A composition for attracting male *Synanthedon scitula*, containing a male *Synanthedon scitula* attracting effective amount of Z,Z-3,13-octadecadienyl acetate, optionally E,Z-2,13-octadecadienyl acetate, optionally Z,E-3,13-octadecadienyl acetate, and optionally a carrier material or carrier; the composition containing less than about 0.3% E,Z-3,13-octadecadienyl acetate based on the molar amount of the Z,Z-3,13-octadecadienyl acetate in the composition. A method for attracting male *Synanthedon scitula* to an object or area, involving treating an object or area with a male *Synanthedon scitula* attracting composition containing a male *Synanthedon scitula* attractant effective amount of Z,Z-3,13-octadecadienyl acetate, optionally E,Z-2,13-octadecadienyl acetate, optionally Z,E-3,13-octadecadienyl acetate, and optionally a carrier material or carrier; the composition containing less than about 0.3% E,Z-3,13-octadecadienyl acetate based on the molar amount of the Z,Z-3,13-octadecadienyl acetate in the composition. A method for inhibiting (antagonizing) male *Synanthedon scitula* attraction to female *Synanthedon scitula*, involving exposing a *Synanthedon scitula* population to a composition containing E,Z-3,13-octadecadienyl acetate in a quantity sufficient to inhibit (antagonize) male *Synanthedon scitula* attraction to female *Synanthedon scitula*, and optionally a carrier material or carrier.

21 Claims, 13 Drawing Sheets

FEMALE SEX PHEROMONE OF THE DOGWOOD BORER (DWB), *SYNANTHEDON SCITULA*, AND ATTRACTION INHIBITOR (ANTAGONIST)

REFERENCE TO RELATED APPLICATION

This application claims the benefit of U.S. Provisional Application No. 60/662,067, filed 14 Mar. 2005, and U.S. patent application Ser. No. 11/372,173, filed 9 Mar. 2006, which are incorporated herein by reference in their entirety.

BACKGROUND OF THE INVENTION

The present invention relates to a composition for attracting male *Synanthedon scitula*, containing a male *Synanthedon scitula* attracting effective amount of Z,Z-3,13-octadecadienyl acetate, optionally E,Z-2,13-octadecadienyl acetate, optionally Z,E-3,13-octadecadienyl acetate, and optionally a carrier material or carrier; the composition containing less than about 0.3% E,Z-3,13-octadecadienyl acetate based on the molar amount of the Z,Z-3,13-octadecadienyl acetate in the composition. The present invention also relates to a method for attracting male *Synanthedon scitula* to an object or area, involving treating an object or area with a male *Synanthedon scitula* attracting composition containing a male *Synanthedon scitula* attractant effective amount of Z,Z-3,13-octadecadienyl acetate, optionally E,Z-2,13-octadecadienyl acetate, optionally Z,E-3,13-octadecadienyl acetate, and optionally a carrier material or carrier; the composition containing less than about 0.3% E,Z-3,13-octadecadienyl acetate based on the molar amount of the Z,Z-3,13-octadecadienyl acetate in the composition.

In addition, the present invention relates to a composition for inhibiting (antagonizing) male *Synanthedon scitula* attraction to female *Synanthedon scitula*, containing E,Z-3,13-octadecadienyl acetate in a quantity sufficient to inhibit male *Synanthedon scitula* attraction to female *Synanthedon scitula*, and optionally a carrier material or carrier. The present invention also relates to a method for inhibiting (antagonizing) male *Synanthedon scitula* attraction to female *Synanthedon scitula*, comprising exposing a *Synanthedon scitula* population to a composition comprising E,Z-3,13-octadecadienyl acetate in a quantity sufficient to inhibit (antagonize) male *Synanthedon scitula* attraction to female *Synanthedon scitula*, and optionally a carrier material or carrier.

In addition, the present invention relates to a method for mass trapping male *Synanthedon scitula*, comprising exposing a *Synanthedon scitula* population to a composition comprising Z,Z-3,13-octadecadienyl acetate, optionally E,Z-2,13-octadecadienyl acetate, and optionally Z,E-3,13-octadecadienyl acetate in a quantity sufficient to reduce the male *Synanthedon scitula* population available to impregnate female *Synanthedon scitula*, and optionally a carrier material or carrier.

In addition, the present invention relates to a method for disrupting male *Synanthedon scitula* mating with female *Synanthedon scitula*, comprising exposing a *Synanthedon scitula* population to a composition comprising Z,Z-3,13-octadecadienyl acetate, optionally E,Z-2,13-octadecadienyl acetate, and optionally Z,E-3,13-octadecadienyl acetate in a quantity sufficient to disrupt male *Synanthedon scitula* mating with female *Synanthedon scitula*, and optionally a carrier material or carrier.

The dogwood borer (DWB), *Synanthedon scitula* (Harris) (*Lepidoptera*: Sesiidae), not only is an important pest of dogwood but also causes severe problems on at least 19 species of fruit, nut, and ornamental trees in the eastern United States and Canada (Bergh, J. C., and T. C. Leskey, Cana. Entomol., 135: 615-635 (2003); Eichlin, T. D., and W. D. Duckworth, Sesioidea: Sesiidae, pp. 1-176, In R. B. Dominick (ed.), The moths of America North of Mexico, fascicle 5.1, Wedge Entomological Research Foundation, Washington, D.C. (1988); Engelhardt, G. P., J. Econ. Entomol., 25: 239-294 (1932)). DWB more recently has become an increasingly economically important pest of apples (Kain, D. and R. W. Straub, N.Y. Fruit. Quart., 9: 10-12 (2001); Riedl, H., et al., Can. Entomol., 117: 1367-1377 (1985); Warner, J., and S. Hay, Can. Entomol., 117: 1471-1478 (1985)). The ultimate factor responsible for the increased abundance of DWB in apples is the use of clonal, size-controlling rootstocks in high-density apple orchards due to international competition in the apple market (Marshall, D. W., and P. K. Andrews, HortTechnology, 4: 1-16 (1994)). Commercially available pheromone lures for dogwood borer rely on generalized sex pheromone components identified from other *Sesiid* species (Nielsen, D. G., et al., EAG and field responses of *sesiid* males to sex pheromones and related compounds, pp. 11-26, In J. W. Neal (ed.), Pheromones of the Sesiidae, SEA, U.S. Dept. Agric., ARR-NE-6, Washington. DC (1979); Tumlinson, J. H., et al.; Science (Wash D.C.), 185: 614-616 (1974)). Unfortunately, the commercially available pheromone lures have produced unreliable results (Bergh, J. C., et al., J. Econ. Entomol., 97: 344-352 (2003); Braxton, S. M., and M. J. Raupp, J. Arbor., 21: 177-180 (1995); Davidson, J. A., et al., J. Arbor., 18: 81-84 (1992); Meyer, W. L., and W. S. Cranshaw, Southwest Entomol., 19: 71-76 (1994); Pfeiffer, D. G., and J. C. Killian, 3. Entomol. Sci., 34: 210-218 (1999); Riedl, H., et al., Cana. Entomol., 117: 1.367-1377 (1985); Snow, J. W., et al., J. Agric. Entomol., 2: 73-84 (1985); Bergh et al., J. Econ. Entomol. 97: 344-352 (2004)). Thus a species-specific sex pheromone is needed for detecting, monitoring, and managing this pest.

SUMMARY OF THE INVENTION

In accordance with the present invention there is provided a composition for attracting male *Synanthedon scitula*, containing a male *Synanthedon scitula* attracting effective amount of Z,Z-3,13-octadecadienyl acetate, optionally E,Z-2,13-octadecadienyl acetate, optionally Z,E-3,13-octadecadienyl acetate, and optionally a carrier material or carrier; the composition containing less than about 0.3% E,Z-3,13-octadecadienyl acetate based on the molar amount of the Z,Z-3,13-octadecadienyl acetate in the composition.

Also in accordance with the present invention, there is provided a method for attracting male *Synanthedon scitula* to an object or area, involving treating an object or area with a male *Synanthedon scitula* attracting composition containing a male *Synanthedon scitula* attractant effective amount of Z,Z-3,13-octadecadienyl acetate, optionally E,Z-2,13-octadecadienyl acetate, optionally Z,E-3,13-octadecadienyl acetate, and optionally a carrier material or carrier; the composition containing less than about 0.3% E,Z-3,13-octadecadienyl acetate based on the molar amount of the Z,Z-3,13-octadecadienyl acetate in the composition.

Still in accordance with the present invention, there is provided a composition for inhibiting (antagonizing) male *Synanthedon scitula* attraction to female *Synanthedon scitula*, containing E,Z-3,13-octadecadienyl acetate in a: quantity sufficient to inhibit (antagonize) male *Synanthedon scitula* attraction to female *Synanthedon scitula*, and optionally a carrier material or carrier.

Also in accordance with the present invention is a method for inhibiting (antagonizing) male *Synanthedon scitula* attraction to female *Synanthedon scitula*, comprising exposing a *Synanthedon scitula* population to a composition comprising E,Z-3,13-octadecadienyl acetate in a quantity sufficient to inhibit (antagonize) male *Synanthedon scitula* attraction to female *Synanthedon scitula*, and optionally a carrier material or carrier.

Also in accordance with the present invention, the present invention relates to a method for mass trapping male *Synanthedon scitula*, comprising exposing a *Synanthedon scitula* population to a composition comprising Z,Z-3,13-octadecadienyl acetate, optionally E,Z-2,13-octadecadienyl acetate, and optionally Z,E-3,13-octadecadienyl acetate in a quantity sufficient to reduce the male *Synanthedon scitula* population available to impregnate female *Synanthedon scitula*, and optionally a carrier material or carrier.

Also in accordance with the present invention, there is provided a method for disrupting male *Synanthedon scitula* mating with female *Synanthedon scitula*, comprising exposing a *Synanthedon scitula* population to a composition comprising Z,Z-3,13-octadecadienyl acetate, optionally E,Z-2,13-octadecadienyl acetate, and optionally Z,E-3,13-octadecadienyl acetate in a quantity sufficient to disrupt male *Synanthedon scitula* mating with female *Synanthedon scitula*, and optionally a carrier material or carrier.

DETAILED DESCRIPTION OF THE INVENTION

Figure 1:
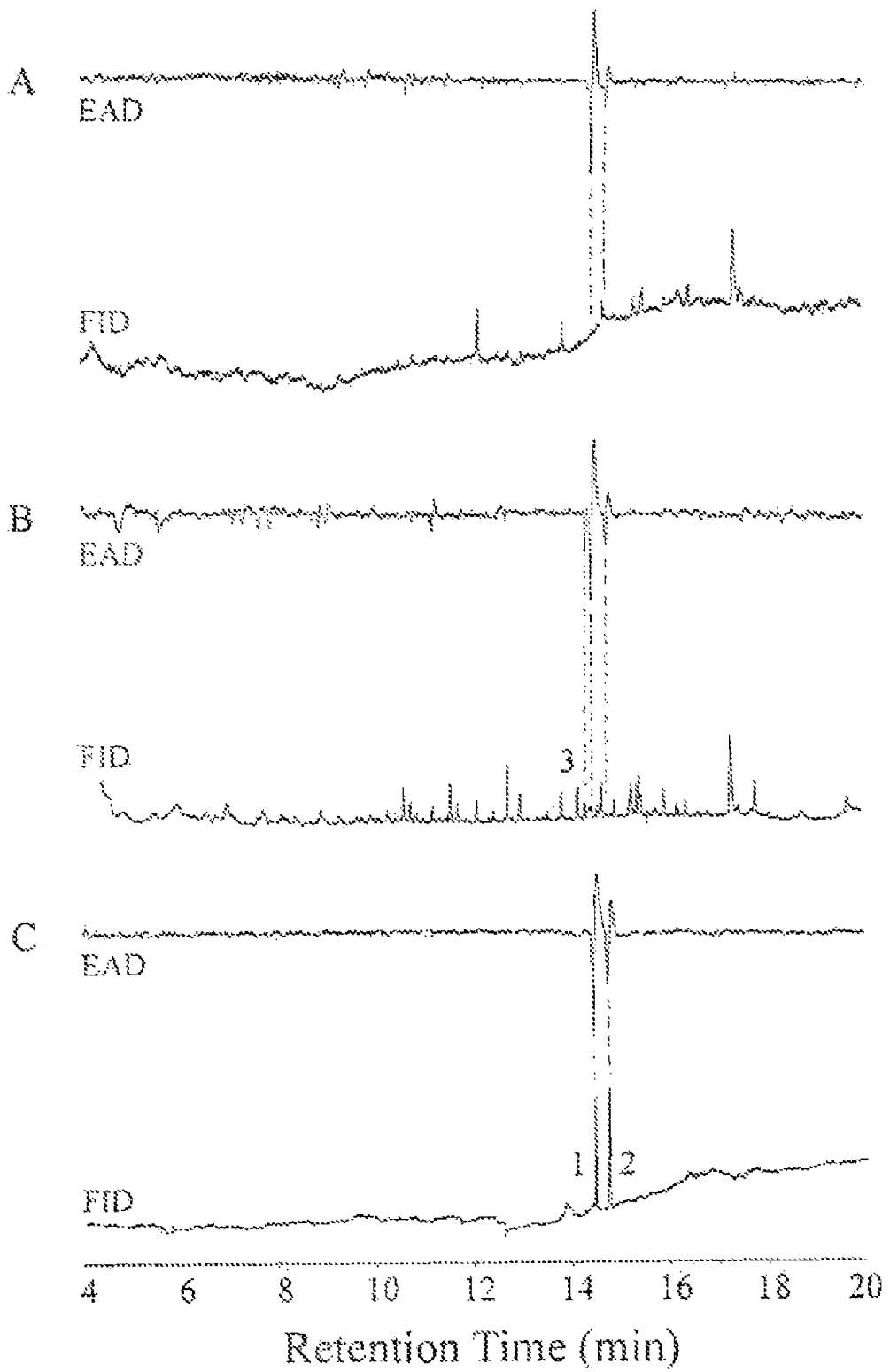
FIG. 1 shows simultaneous EAD and FID responses of an adult male DWB antenna to (A) gland extracts from 2 virgin female DWB (3- and 5-day-old); (B) effluvia trapped for 48 h from 7 virgin female DWB (3- to 13-day-old); and (C) synthetic ZZ 3,13-ODDA and EZ 2,13-ODDA (1 ng each, 1:1 ratio, v/v). Identification of peaks: 1, ZZ 3,13-ODDA; 2, EZ 2,13-ODDA; and 3, ZE 3,13-ODDA.

The compounds described herein (e.g., Z,Z-3,13-octadecadienyl acetate, E,Z-2,13-octadecadienyl acetate, Z,E-3,13-octadecadienyl acetate, and E,Z-3,13-octadecadienyl acetate) may be applied with a carrier component or carrier (e.g., agronomically or physiologically or pharmaceutically acceptable carrier). The carrier component can be a liquid or a solid material. As is known in the art, the vehicle or carrier to be used refers to a substrate such as a membrane, hollow fiber, microcapsule, cigarette filter, gel, polymers, septa, or the like. All of these substrates have been used to release insect pheromones in general and are well known in the art. Suitable carriers are well-known in the art and are selected in accordance with the ultimate application of interest. Agronomically acceptable substances include aqueous solutions, glycols, alcohols, ketones, esters, hydrocarbons halogenated hydrocarbons, polyvinyl chloride; in addition, solid carriers such as clays, cellulosic and rubber materials and synthetic polymers. The carrier or carrier material as used herein is defined as not including the body of an insect (e.g., *Synanthedon scitula*).

The amount of the composition for attracting male *Synanthedon scitula* used will be at least an effective amount. The term "effective amount," as used herein, means the minimum amount of the composition needed to attract male *Synanthedon scitula* to a treated area or object or locus when compared to the same area or object or locus which is untreated. Of course, the precise amount needed will vary in accordance with the particular composition used; the type of area or object to be treated; the number of days of attractiveness needed; and the environment in which the area or object or locus is located. The precise amount of the composition can easily be determined by one skilled in the art given the teaching of this application. For example, one skilled in the art could follow the procedures utilized below; the composition would attract more than 50% of the male *Synanthedon scitula* and would be statistically significant in comparison to a control. Preferably for compositions containing Z,Z-3,13-ODDA and E,Z-2,13-ODDA (but not Z,E-3,13-ODDA) (binary blend) the molar ratio of Z,Z-3,13-ODDA:E,Z-2,13-ODDA is about 99.5:about 0.5 to about 90:about 10 (e.g., 99.5:0.5 to 99:10); more preferably the molar ratio is about 94:about 6 (e.g., 94:6). Preferably for compositions containing Z,Z-3,13-ODDA, E,Z-2,13-ODDA, and Z,E-3,13-ODDA (trinary blend), the molar ratio of Z,Z-3,13-ODDA: E,Z-2,13-ODDA:Z,E-3,13-ODDA is about 80:about 10:about 10 to about 99:about 0.5:about 0.5 (e.g., 80:10:10 to 99:0.5:0.5); more preferably the molar ratio is about 88:about 6:about 6 (e.g., 88:6:6). Effective loadings of the attractant in the compositions (used, for example, for monitoring purposes) may vary between about 0.1 to about 10 (e.g., 0.1-10) mg/septum (preferably about 0.3-about 5 (e.g., 0.3-5) mg/septum, more preferably about 0.5-about 1 (e.g., 0.5-1) mg/septum)). For the above pheromone compositions which attract male *Synanthedon scitula*, the amount of E,Z-3,13-ODDA must not exceed about 0.3% (e.g., ≦0.3% or <0.3%) based on the molar amount of the Z,Z-3,13-ODDA in the composition (preferably the composition contains less than about 0.25% (e.g., ≦0.25% or <0.25%), more preferably less than about 0.2% (e.g., ≦0.2% or <0.2%), more preferably less than about 0.15% (e.g., ≦0.15% or <0.15%), more preferably less than about 0.1% (e.g., ≦0.1% or <0.1%), more preferably less than about 0.05% (e.g., ≦0.05% or <0.05%), most preferably about 0% (e.g., 0%).

The compositions described herein may or may not contain a control agent for *Synanthedon scitula*, such as a biological control agent or an insecticide known in the art to kill *Synanthedon scitula*. Other compounds may be added to the composition provided they do not substantially interfere with the intended activity of the composition; whether or not a compound interferes with attractant activity can be determined, for example, by the procedures utilized below.

In the case where the desired response is inhibiting (antagonizing) male DWB attraction to female DWB or female sex pheromone through the use of E,Z-3,13-octadecadienyl acetate, an "effective amount" is defined as that quantity of E,Z-3,13-octadecadienyl acetate which prevents male DWB from orienting to the female DWB (and inseminating the female DWB); in other words, an effective amount is a quantity sufficient to prevent potential mates from finding each other, thus inhibiting (antagonizing) male DWB attraction to female dogwood borers or reducing the probability that the dogwood borers will mate. Factors such as population density, temperature, wind velocity and release rate will influence the actual number of DWB inhibited (antagonized). The precise amount of the composition can easily be determined by one skilled in the art given the teaching of this application. For example, the exact dose to use in any particular set of circumstances can readily be determined by a dose response field test or one skilled in the art could follow the procedures utilized below; the composition would inhibit (antagonize) male DWB attraction to female DWB or female sex pheromone by more than 50% and would be statistically significant in comparison to a control. Preferably the composition contains at least 0.5% by weight E,Z-3,13-octadecadienyl acetate (or at least 0.5% based on the molar amount of the Z,Z-3,13-ODDA in the composition). Effective loadings of the E,Z-3,13-ODDA in the composition may vary between about 1 to about 100 (e.g., 1-100) mg/dispenser (preferably about 1-about 50 (e.g., 1-50) mg/dispenser, more preferably about 10-about 30 (e.g., 10-30) mg/dispenser). The composition may or may not contain a control agent for *Synanthedon scitula*, such as a biological control agent or an insecticide known in the art to kill *Synanthedon scitula*. Other compounds may be added to the composition provided they do not substantially interfere with the intended activity of the composition; whether or not a compound interferes with inhibiting (antagonizing) male DWB attraction to female DWB or female sex pheromone can be determined, for example, by the procedures utilized below.

In the case where the desired response is disrupting male DWB mating with female DWB through the use of a composition containing Z,Z-3,13-octadecadienyl acetate, optionally E,Z-2,13-octadecadienyl acetate, optionally Z,E-3,13-octadecadienyl acetate, and optionally a carrier material or carrier (the composition optionally containing less than about 0.3% E,Z-3,13-octadecadienyl acetate based on the molar amount of the Z,Z-3,13-octadecadienyl acetate in the composition), an "effective amount" is defined as that quantity of Z,Z-3,13-octadecadienyl acetate, optionally E,Z-2,13-octadecadienyl acetate, and optionally Z,E-3,13-octadecadienyl acetate which confuse male DWB from orienting to the female DWB (and inseminating the female DWB); in other words, an effective amount is a quantity sufficient to prevent potential mates from finding each other, thus impeding or disrupting the ability of the dogwood borers to mate. Alternatively, the "effective amount" is defined as that quantity of Z,Z-3,13-octadecadienyl acetate, optionally E,Z-2,13-octadecadienyl acetate, and optionally Z,E-3,13-octadecadienyl acetate which prevents male DWB from orienting to the female DWB and inseminating the female DWB at a rate significantly higher than non-treated location. Factors such as population density, temperature, wind velocity and release rate will influence the actual number of DWB disrupted. The precise amount of the composition can easily be determined by one skilled in the art given the teaching of this application. For example, the exact dose to use in any particular set of circumstances can readily be determined by a dose response field test. Effective loadings of the Z,Z-3,13-octadecadienyl acetate, optionally E,Z-2,13-octadecadienyl acetate, optionally Z,E-3,13-octadecadienyl acetate, and optionally a carrier material or carrier (the composition optionally containing less than about 0.3% E,Z-3,13-octadecadienyl acetate based on the molar amount of the Z,Z-3,13-octadecadienyl acetate in the composition) may vary between about 50 to about 150 (e.g., 50-150) mg/dispenser (preferably about 80-about 100 (e.g., 80-100) mg/dispenser. The composition may or may not contain a control agent for *Synanthedon scitula*, such as a biological control agent or an insecticide known in the art to kill *Synanthedon scitula*. Other compounds may be added to the composition provided they do not substantially interfere with the intended activity of the composition; whether or not a compound interferes with mating disrupting activity can be determined, for example, by the procedures utilized with other *Sesiid* species, peachtree borer (PTB) *S. exitiosa* (say) and lesser peachtree borer (LPTB) *S. pictipes* (Grote and Robinson) (Agnello, A. M., and D. P. Kain, N.Y. Fruit Quar., 10: 29-31 (2002); Gentry, C. R., and J. W. Snow, J. Ga. Entomol. Soc., 19: 350-356 (1984); Pfeiffer, D. G., et al., J. Econ. Entomol., 84: 218-223 (1991)).

Other compounds may be added to the compositions described herein provided they do not substantially interfere with the intended activity of the composition.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Insects: Larvae of DWB were excavated from burr knot tissue of apple trees (Jefferson and Berkeley Counties, WV, and Frederick County, VA) with obvious signs of infestation including frass and entry wounds in October and November. Larvae were brought back to the laboratory and reared on general purpose Lepidopteran diet (Bioserv, Frenchtown N.J.) in an incubator at 25° C. (16L:8D) until pupation. Pupae were sexed according to the characteristics described by Leskey and Bergh (Leskey, T. C., and J. C. Bergh, Florida Entomol., 36: 379-381 (2003)) and held in 1 oz. clear plastic cups (Jet Plastica Industries, Hatfied Pa.) with a small piece of moistened cotton dental wick and topped with plastic caps. Pupae were then shipped by express carrier or delivered to Beltsville, Md. in January. Upon arrival, the pupae were kept in a in an insectary at 25° C. and 16L:8D photoperiod until adult emergence. Absorbent cotton moistened with 8% sugar water was provided as food source for emerged moths. Moths were sexed and females were transferred to effluvial collection device for volatiles collection.

Effluvial Collections: Volatiles were collected using six groups of 1- to 13-day-old virgin females (3 to 10 females per group) at room temperature and 16L:8D photoperiod. The moths were separately introduced into three 1-1, 4-necked glass containers (Zhang, A., et al., J. Chem. Ecol., 20: 2415-2427 (1994)). Air was drawn into the container through 6-14 mesh activated charcoal (Fisher Scientific, Pittsburgh, Pa.), and out of the container through two traps (15 cm×1.5-cm o.d.) containing Super Q (200 mg each; Alltech Associates, Inc., Deerfield, Ill.) by vacuum (~1 l/min). Female moths were fed with 10% sugar solution on cotton balls and aerated continuously for 3-7 days at room temperature and 16L:8D photoperiod. The adsorbent traps were changed every 48 hr. Adsorbents were eluted with methylene chloride (4×0.5 ml); the eluates (2 ml/each sample) were concentrated to ~20 µl under a nitrogen stream and stored at −30° C. for future analysis.

Pheromone Gland Extractions: Pheromone gland extracts were obtained during photophase from six groups of 2- to 13-day-old virgin females that had been used in aeration. A female abdomen was compressed gently until the ovipositor everted from the abdominal tip. The ovipositor was then excised with micro scissors into a conical glass vial containing ~100 µl methylene chloride-methanol (3:1). The glands were soaked for at least 2 hr at room temperature. The extracts were then removed, and the glands were re-extracted with 100 µl methylene chloride-methanol. The combined solution was concentrated to ~20 µl under nitrogen stream and kept at −30° C. in a freezer for future analysis.

Electrophysiological. Recordings and Mass Spectrometry: The coupled gas chromatographic-electroantennographic detection (GC-EAD) system used was as previously described (Zhang, A., and S. Polavarapu, J. Chem. Ecol., 29: 2153-2164 (2003); Zhang, A., and S. Polavarapu, J. Chem. Ecol., 30: 1531-1545 (2004); Zhang, A., et al., J. Chem. Ecol., 23: 231-245 (1997)). A Hewlett Packard (HP) 6890 gas chromatograph equipped with a 60 m×0.25-mm i.d., 0.25-mm film-thickness DB-WAXETR capillary column (J&W Scientific Inc., Folsom, Calif., 120° C. for 2 min, then programmed to 250° C. at 10° C./min and held for 10 min) or a 60 m×0.25-mm i.d., 0.25-mm film-thickness DB-5 capillary column (J&W Scientific Inc., 100° C. for 2 min, then programmed to 250° C. at 15° C./min and held for 10 min) in the splitless mode with hydrogen as carrier (1.4 ml/min) was used for GC-EAD analysis. Electronic impact (EI) gas chromatography-mass spectrometry (GC-MS) was conducted on a Hewlett-Packard 6890 GC coupled to a HP 5973 Mass Selective Detector using an identical DB-WAXETR capillary column (120° C. for 2 min, then programmed to 230° C. at 15° C./min and held for 25 min for regular analysis, but with helium as carrier gas. A 70 eV electron beam was employed for sample ionization.

Chemicals: (Z,Z)-3,13-octadecadienyl acetate was purchased from Bedoukian Research, Danbury Conn. (~90% purity). It was purified by flush chromatography using 2:10 of $CH_2Cl_2$:hexane as the mobile phase on 15% $AgNO_3$ in silica gel 60 (EM Science, 230-400 mesh). The fractions with the impurity of E,Z-3,13-ODDA less than 0.3% based on the molar amount of the Z,Z-3,13-octadecadienyl acetate were combined and solvents were evaporated using a Büchi RE 111 rotary evaporator. All other synthetic pheromone standards were purchased from Pheromone Bank, Wageningen, The Netherlands (>96% purity). Purities of chemicals were checked on a 60 m polar DB-WAXETR GC capillary column before preparing the lures for the field study.

Lure Analysis: The binary and trinary lures exposed in the field during 6 wk, 8 wk, and 12 wk were collected and placed individually into 20 ml hexane in a 25 ml vial and soaked for 48 hr. GC analyses of pheromone lures were conducted on a HP 6890 GC coupled to a DB-5 capillary column by injecting of 1 ml of each extract. The pure Z,Z-3,13-ODDA were used as the standard and remaining pheromone concentrations were obtained by comparison with this standard at the same conditions.

Field Trapping Tests: Red natural rubber septa (5 mm, Wheaton, N.J.) loaded with the desired rates of Z,Z-3,13-ODDA and the blends in ~20 ml of hexane solution were used for field deployment. The same amount of solvent (hexane) was loaded on the septum for the blank control. After loading, the solvent was allowed to evaporate in a fume hood for 30 min. Lures were then wrapped in aluminum foil, stored in 20 ml plastic vials, and shipped by express carrier on the same day. Upon arrival, the lures were kept in a freezer at −10° C. until deployed. All field tests were conducted in commercial apple fields in WV, VA, and NC using Pherocon 1C or Delta sticky traps (Trécé, Salinas, Calif.). Traps were placed in trees at ~1.2 m above the ground (Riedl, Fla., et al., Cana. Entomol., 117: 1367-1377 (1985)). At each location, experimental lures were randomized within each of three to five rows (depending on the number of replicates per test) and separated by at least one buffer row, and traps were spaced at a minimum of ~25 m intervals within a row. Traps were rotated among positions within each row at weekly intervals for the duration of each test. The number of dogwood borer, peachtree borer, lilac borer, and other male Sesiidae moths captured were recorded weekly. In the first comparison trial, the following lures were deployed: the single component (100% Z,Z-3,13 ODDA); the binary blend (Z,Z-3,13-ODDA:E,Z-2, 13-ODDA=94:6); a second two-component blend (Z,Z-3,13-ODDA:Z,E-3,13-ODDA=94:6, based on the molar amount of the Z,Z-3,13-octadecadienyl acetate in the composition); the trinary blend (Z,Z-3,13-ODDA:E,Z-2,13-ODDA:Z,E-3, 13-ODDA=88:6:6); and control. Next, to evaluate the attractive effect of addition of third component, 0.5, 1, 3, or 10% based on the molar amount of the Z,Z-3,13-octadecadienyl acetate of Z,E-3,13-ODDA were added into the binary blend individually. Similarly, 0.5, 1, 3, or 10% of E,Z-2,13-ODDA were individually added into a blend consisted of Z,Z-3,13-ODDA:Z, E-3,13-ODDA (94:6) to evaluate the effect of E,Z-2,13-ODDA. In another comparison, 0.5, 1, 2, or 3% E,Z-3, 13-ODDA was added to the trinary blend. Dose response tests of the trinary and binary blends were deployed in each location, with doses consisting of 10-μg, 100-μg, 300-μg, 1-mg, and 10-mg (trinary blend); and 10-μg, 100-μg, 300-μg, 500-μg, and 1-mg (binary blend), respectively. Caged live virgin females (2-4 days old and 1 female per cage) were deployed in traps to provide a natural source of pheromone for comparison with traps baited with the binary and trinary blends. In a final comparison to determine over what distance DWB can detect the trinary blend, we compared captures in traps baited with the trinary blend deployed within an infested apple orchard, and 50 and 100 in outside the orchard within a large wood lot habitat.

Statistics: The data on control traps were omitted in the analysis because of zero trap catches. Unless otherwise specified, data on trap catches from each test were logarithm transformed (log χ+1) to normalize the variance before analysis. Means were compared by one-way analysis of variance (ANOVA) followed by Ryan-Einot-Gabriel-Welsch Range test (SPSS 10.0 for Windows, George and Mallery, 2002) for significance at α=0.05.

Results. Analysis of Sex Pheromone Components in Female Effluvial Collections and Gland Extracts: A typical coupled GC-EAD graph is showed in FIG. 1, exhibiting two EAD-active responses in female gland extract (1A) and three EAD-active responses in effluvial collection extract (1B). Among those responses, peak 1 and peak 2 coincided with Z,Z-3,13-ODDA and E,Z-2,13-ODDA, respectively, in GC retention times on both capillary columns (Table 1), and EAD-activities of Z,Z-3,13-ODDA and E,Z-2,13-ODDA were confirmed by synthetic standards (1C). When a combined gland extract (20 females) was analyzed by GC-MS with select ion monitoring of the ion m/z 248 (M-60), only two peaks appeared at 15.61 and 16.13 min with a ratio of 94:6. The identity of Z,Z-3,13-ODDA at 15.61 min and E,Z-2,13-ODDA at 16.13 min was confirmed by synthetic standards in GC-MS. However, the EAD-active peak 3 from effluvial collection extract, which was sometimes observed in GC-EAD, had never been detected in gland extract with select ion monitoring. GC-EAD analysis of four synthetic geometric isomers of 3,13-ODDA revealed all to have significant. EAD activity (Table 1). Retention time of the Z,E-3,13-ODDA was identical to that of peak 3 on both capillary columns. Therefore, the EAD-active minor component in the effluvial collection extract (peak 3) was determined to be Z,E-3,13-ODDA and the trinary blend ratio was estimated to be 88:6:6 (Z,Z-3,13-ODDA:E,Z-2,13-ODDA:Z,E-3,13-ODDA).

Field Trapping Tests: Male trap captures from initial field studies using septa containing 1-mg of the single-component, the binary blend, a two-component blend, and the trinary blend are summarized in FIG. 2. Adult captures in pheromone traps were likely influenced by level of infestation in a particular orchard, climatic factors during the flight season, as well as other factors including intensity of pest management regimes found within a particular orchard. However, the trap captures from three states all indicated that the major sex pheromone component, Z,Z-3,13-ODDA, itself was surprisingly attractive. Surprisingly, the binary blend of Z, Z-3,13-ODDA with 1~3% of E, Z-2,13-ODD, was significantly more attractive than the single-component. The addition of third minor component, Z,E-3,13-ODDA to create the so-called trinary blend surprisingly enhanced attraction of binary blend significantly. Furthermore, there was no difference between captures in Pherocon 1C (in NC and WV) and Delta sticky traps (in VA).

Figure 3:
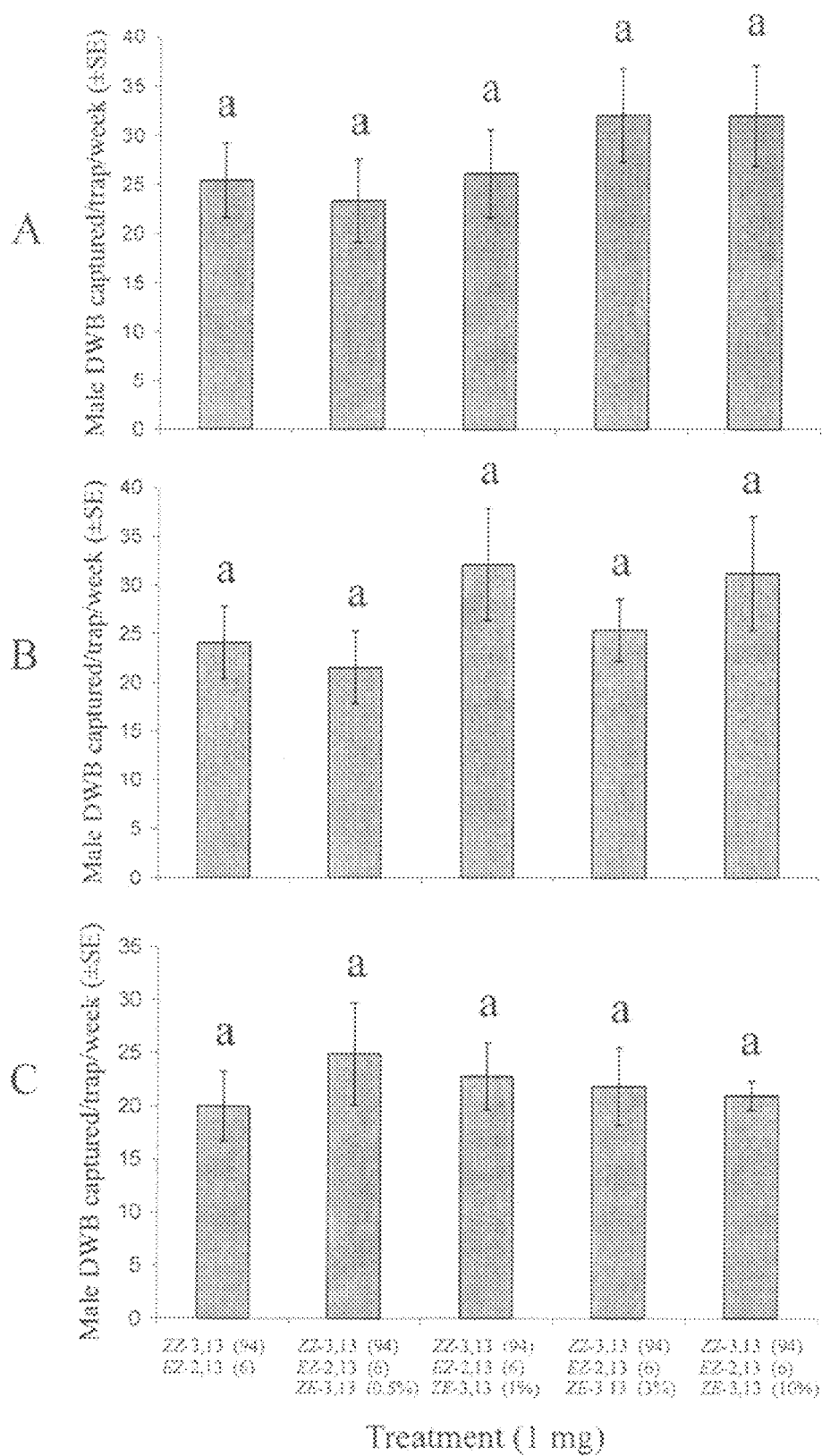
FIG. 3 shows results of DWB pheromone tests (different amounts of Z,E-3,13-octadecadienyl acetate) conducted as follows: (A) from July to August in NC, total number of male DWB trapped was 2,915, $N=21$, $df=4,100$, $F=0.794$, $p=0.532$; (B) from July to August in VA, total number of male DWB trapped was 2,016, $N=15$, $df=4,70$, $F=1.017$, $p\ 0.405$; (C) from June to July in WV, total number of male DWB trapped was 1,659, $N=15$, $df=4,70$, $F=0.300$, $p=0.877$. Bars superscripted by different letters are statistically different (no transformation was performed).
Figure 4:
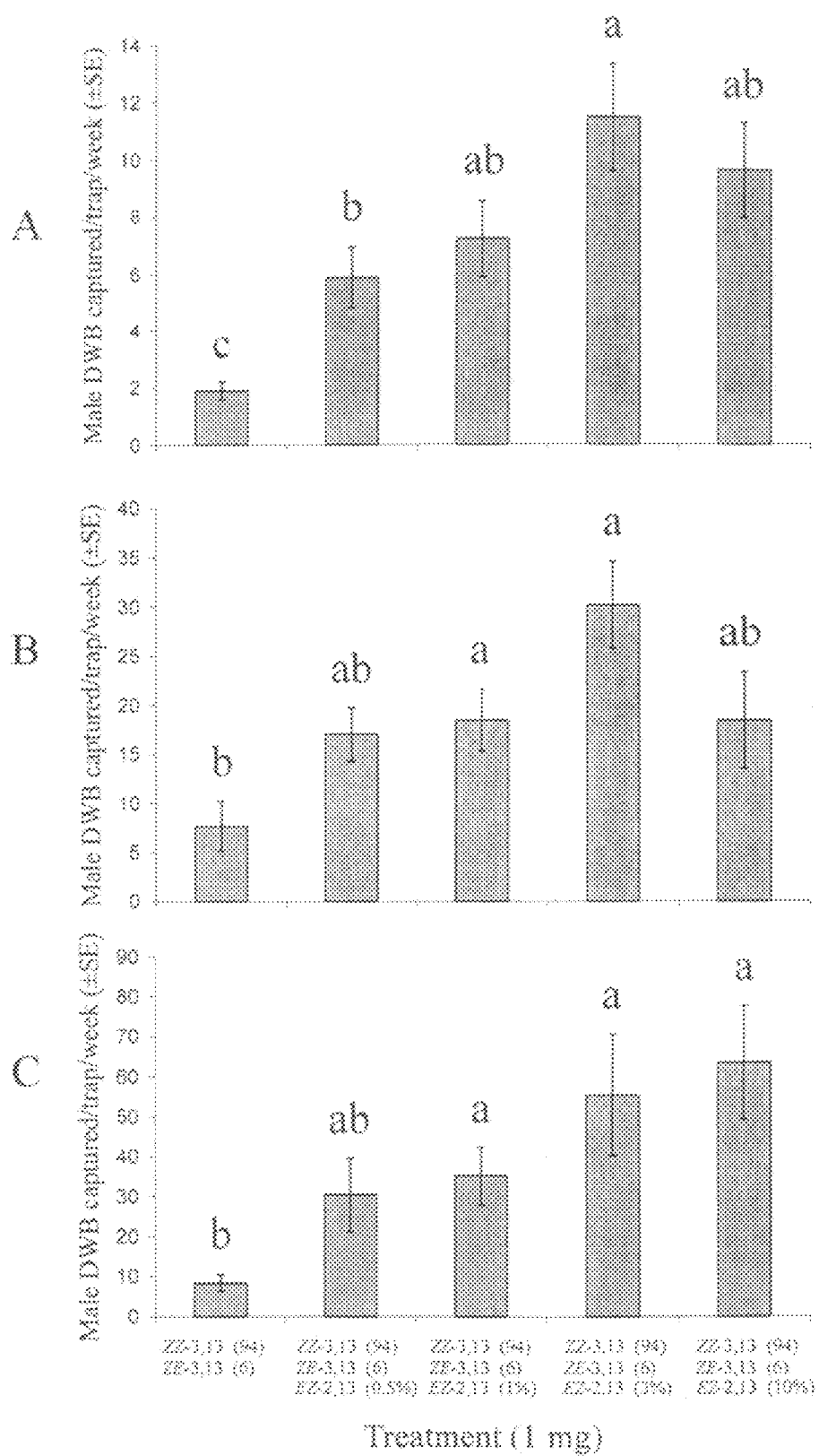
FIG. 4 shows results of DWB pheromone ratio tests (different amounts of E,Z-2,13-octadecadienyl acetate) conducted as follows: (A) from July to August in NC, total number of male DWB trapped was 724, $N=21$, $df=4,100$, $F=9.73$; (B) from July to August in VA, total number of male DWB trapped was 1,375, $N=15$, $df=4,70$, $F=6.01$; (C) from June to July in WV, total number of male DWB trapped was 2,887, $N=15$, $df=4,70$, $F=6.58$. Bars superscripted by different letters are statistically different ($p<0.05$).

Addition of 0.5 to 10% of Z,E-3,13-ODDA to the binary blend did not cause a significant increase in attraction to the binary blend (FIG. 3). However, surprisingly when 0.5 to 10% of E,Z-2,13-ODDA were added to a blend that contains Z,Z-3,13-ODDA and Z,E-3,13-ODDA (94:6), level of attraction to males was significantly increased (FIG. 4).

Figure 5:
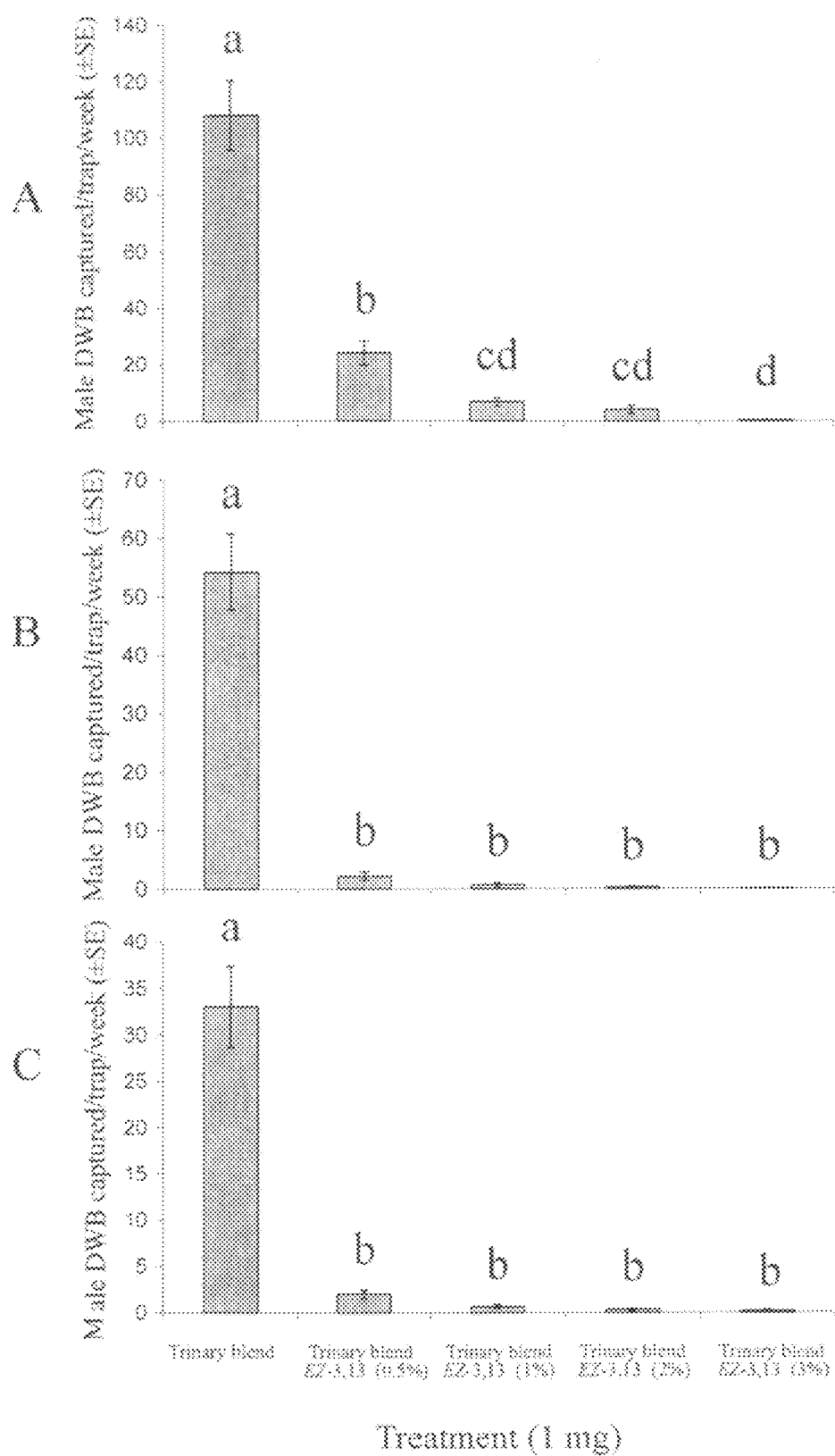
FIG. 5 shows results of DWB attraction antagonistic tests (trinary blend with different amounts of E,Z-2,13-octadecadienyl acetate) conducted as follows: (A) from July to August in NC, total number of male DWB trapped was 2,568, $N=18$, $df=4,85$, $F=83.852$; (B) from July to August in VA, total number of male DWB trapped was 861, $N=15$, $df=4,70$, $F=156.66$; (C) from June to July in WV, total number of male DWB trapped was 1,086, $N=30$, $df=4,145$, $F=181.37$. Bars superscripted by different letters are statistically different ($p<0.05$).

In the consequent test we found that a geometric isomer, E,Z-3,13-ODDA, surprisingly reduced trap captures of DWB significantly. Surprisingly, captures in traps baited with our most attractive lure (trinary blend) were surprisingly significantly inhibited (antagonized) by addition of as little as 0.5-1% E,Z-3 μl 3-ODDA (FIG. 5).

Data from dose response tests with the trinary blend demonstrated that male DWB catches were significantly lower in traps baited with 10-:g compared to captures in traps baited with any other doses tested. When dose was increased to 1-mg and above, trap captures were significantly higher compared to 100-300-:g doses (FIG. 6) in the most locations. In the dose response testes using the binary blend, male DWB captures were significantly greater in traps baited with 300-:g compared to captures in traps baited with 100-:g and lower doses. But captures were not significantly different in traps baited with 300-:g compared to higher doses (FIG. 7).

Figure 8:
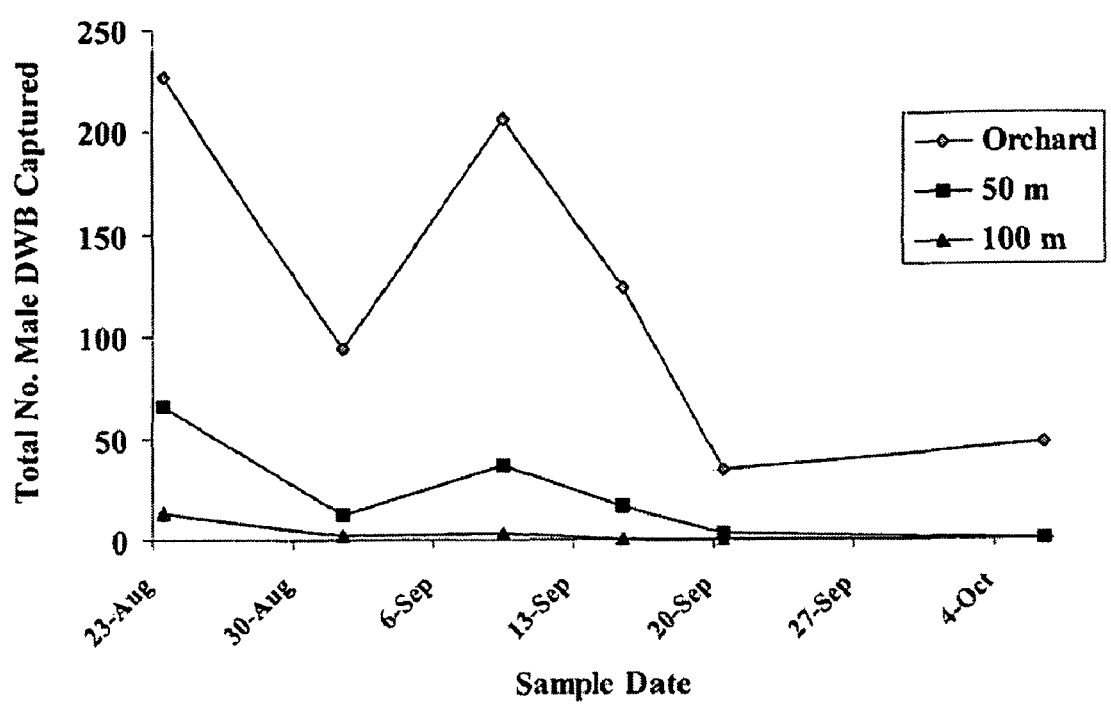
FIG. 8 shows total number of male DWB captured in traps located within a highly infested apple orchard and at 50 and 100 m away from the orchard in a large wood lot from August to October.

Male DWB were attracted to traps baited with the trinary blend at distances of at least 50 m away from a highly infested orchard (FIG. 8). In this comparison, 83% of the captures were based on males recovered from a trap placed within the orchard, 15% were from a trap located 50 m from the orchard, and only 2% of captures consisted of males recovered from a trap at 100 m from the orchard.

Figure 9:
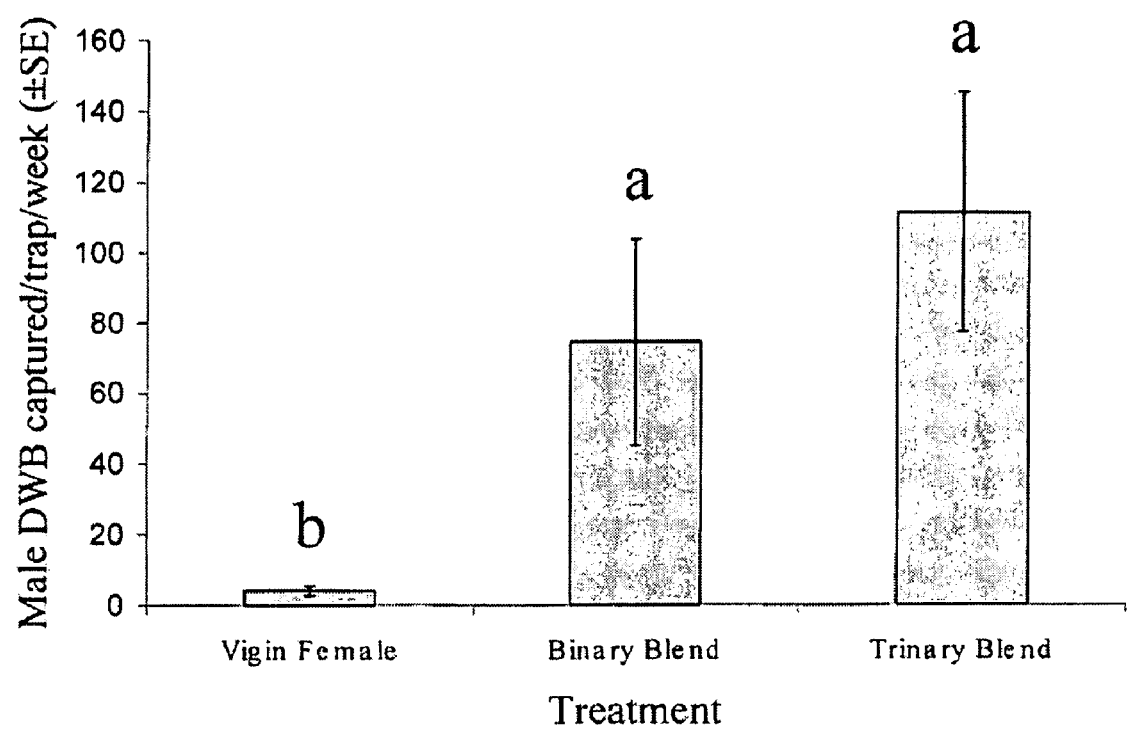
FIG. 9 shows results of DWB pheromone and virgin female comparison tests conducted from August to September in WV; total number of male DWB trapped was 763, $N=4$, $df=2,9$, $F=25.72$. Bars superscripted by different letters are statistically different ($p<0.05$).
Figure 10A:
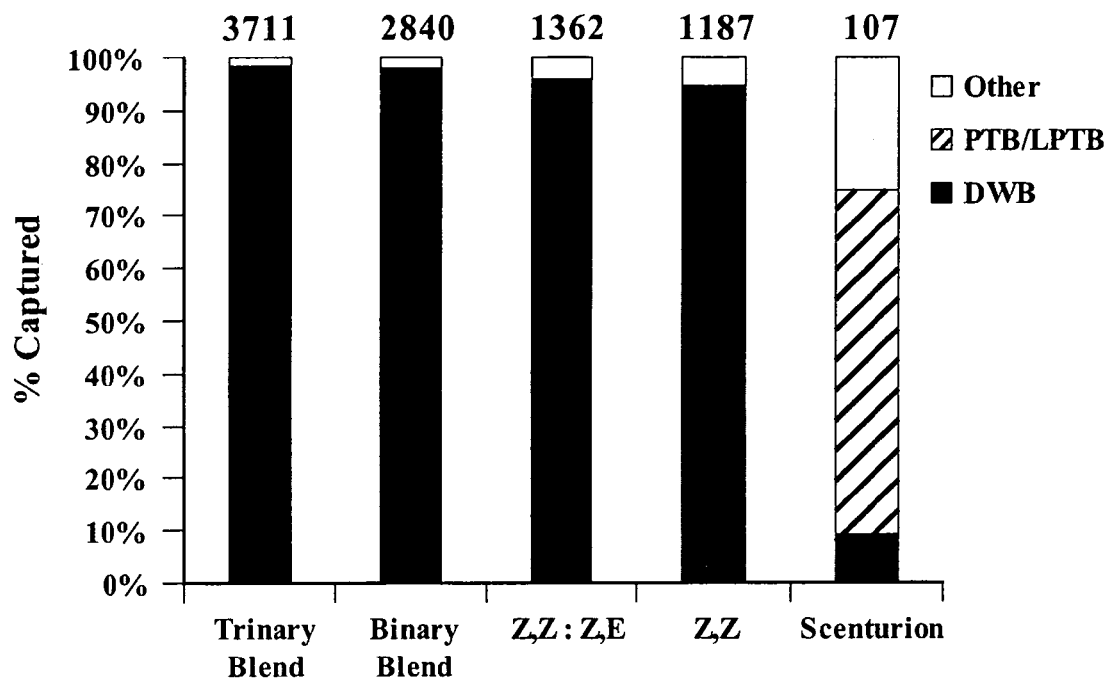
FIG. 10 shows specificity of experimental lures including single component (Z,Z-3,13-ODDA), 2-component (Z,Z-3,13-ODDA:Z,E-3,13-ODDA=94:6 molar ratio), the binary blend (Z,Z-3,13-ODDA:E,Z-2,13-ODDA=94:6), and the trinary blend (Z,Z-3,13-ODDA:E,Z-2,13-ODDA:Z,E-3,13-ODDA=88:6:6) compared with the most attractive commercially available lure based on percentage of dogwood borer (DWB), lesser peachtree borer (LPTB), peachtree borer (PTB), and Other sesiid captured across all locations.
Figure 10B:
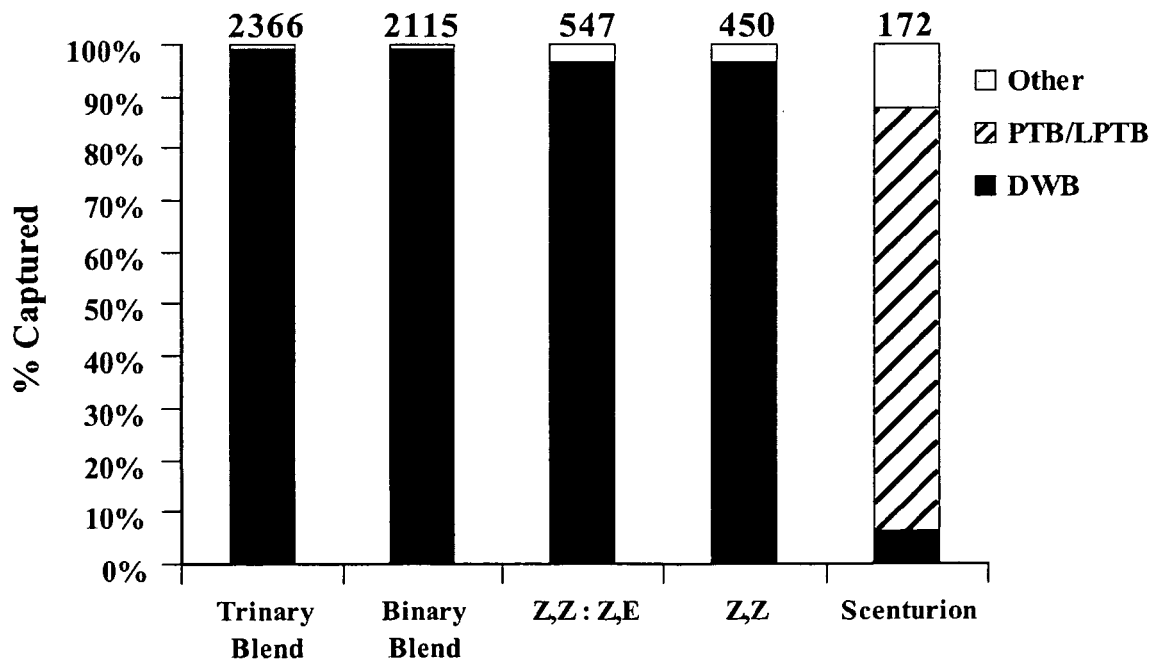
Figure 10C:
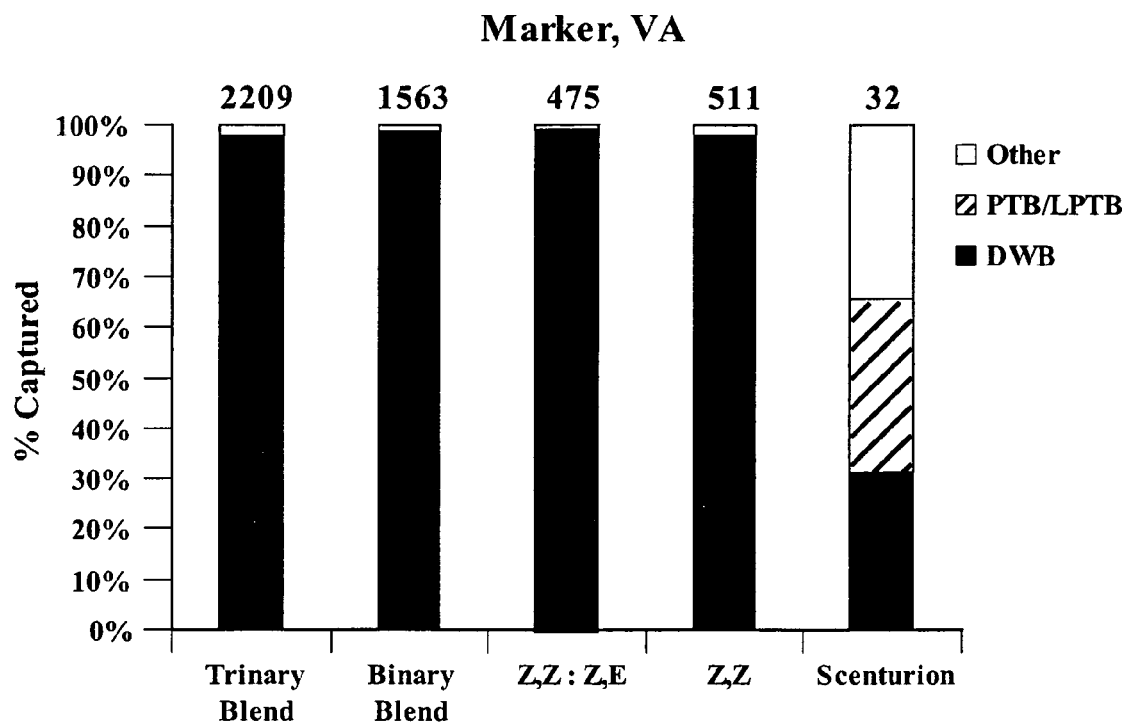
Figure 10D:
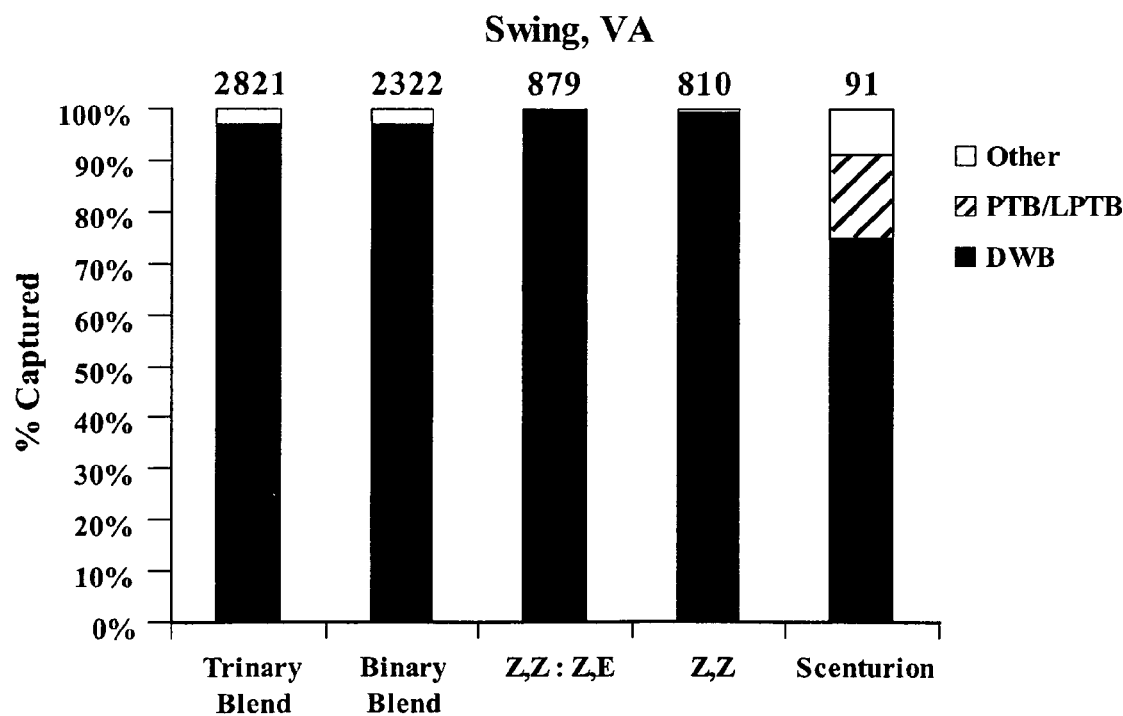
Figure 10E:
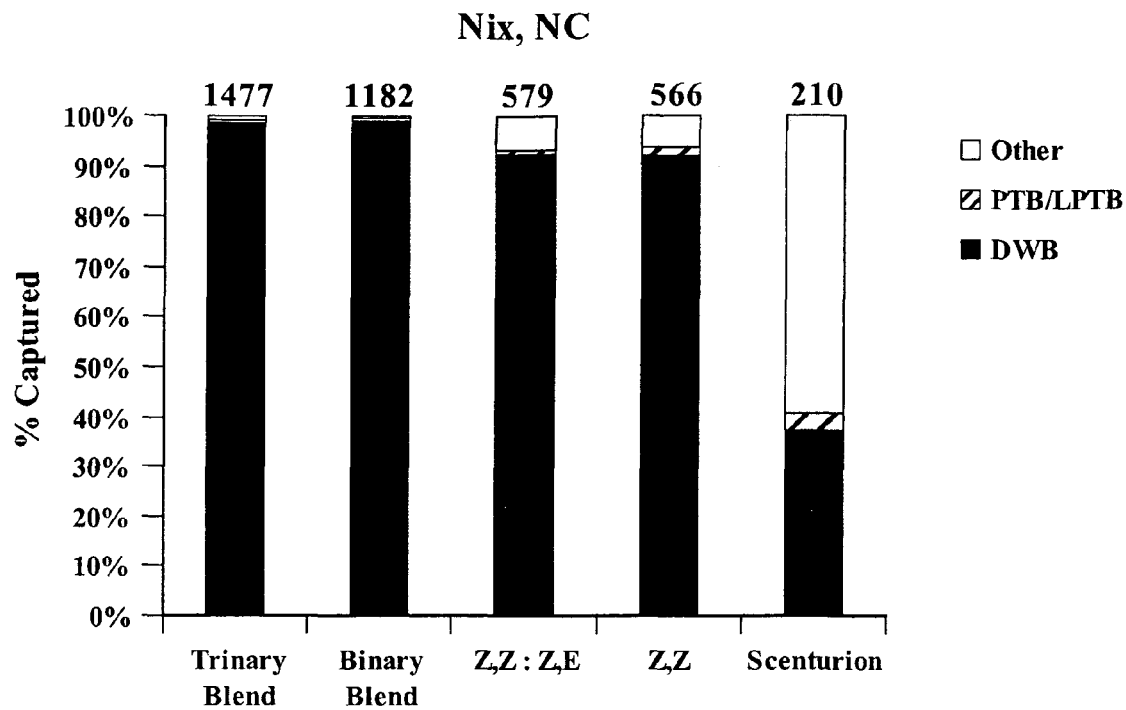
Figure 10F:
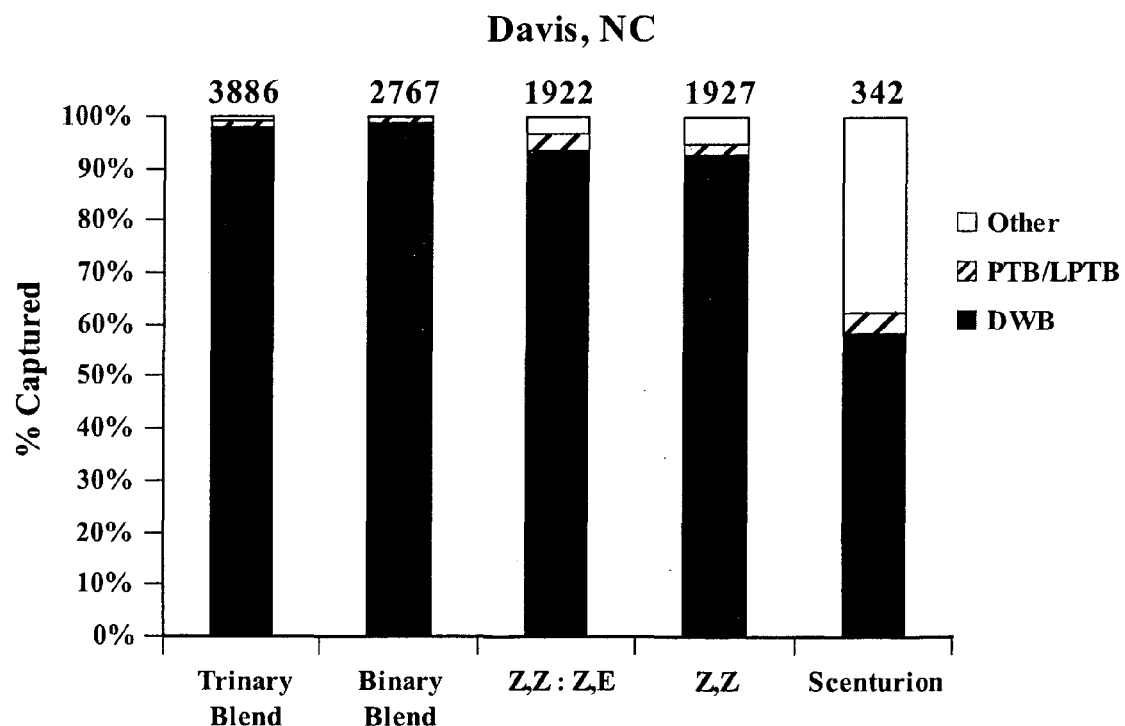
Figure 11:
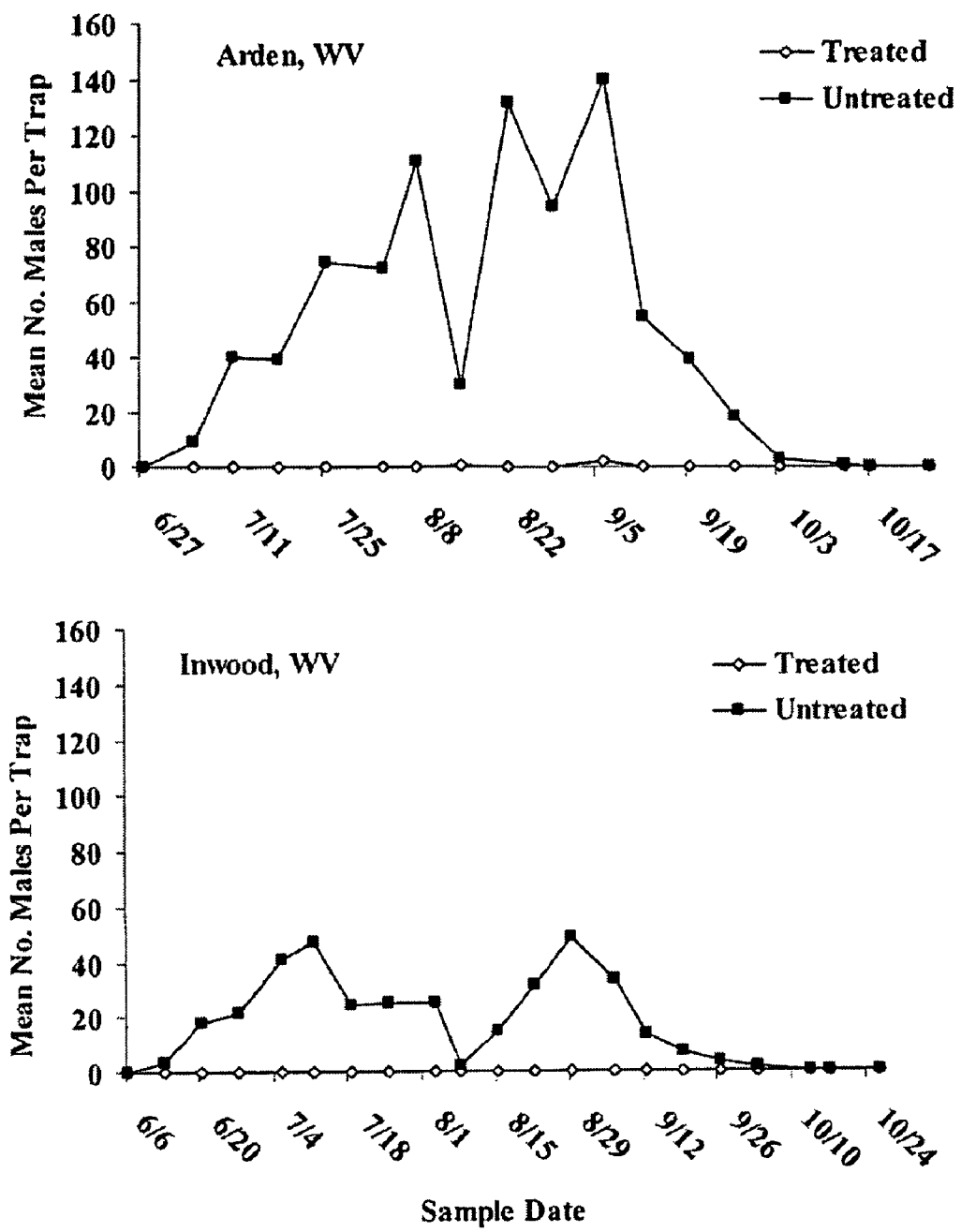
FIG. 11 shows mean number of males captured per week in monitoring traps baited with complete pheromone blend deployed in blocks treated with a behavioral antagonist or left untreated in two commercial orchards in West Virginia.

In the final field test, we evaluated the efficacy of the binary and trinary blends compared to a virgin female. Surprisingly, rubber septa loaded with 1-mg dose of the binary and trinary blends attracted significantly more males than traps baited with one virgin female (FIG. 9).

Species-specificity of experimental blends was surprisingly high. Male dogwood borers represented from 97.1-99.2% of captures with the trinary blend and from 97.8-99.2% of captures with the binary blend across all sites (FIG. 10). Even the less attractive experimental blends were very specific for dogwood borer. Specificity of the Z,Z-3,13-ODDA:Z,E-3,13-ODDA blend and the single component Z,Z-3,13-ODDA for dogwood borers ranged from 92.6-100% and 92-99.6%, respectively, across all sites (FIG. 10). In contrast, the Scenturion® dogwood borer lure was much less species-specific. The percentage of captures comprised of dogwood borers in traps baited with Scenturion® lure ranged from 6.3% in Arden, W. Va. to 74.4% in Winchester, Va. (FIG. 10). Most of the captures in traps baited with Scenturion® lure were peachtree and lesser peachtree borer males at Inwood, W. Va. (65.4%) and at Arden, W. Va. (81.3%). At Nix, N.C., captures of others species included the southern oak borer and the lilac/ash borer, comprising 59.5% of the captures in traps baited with Scenturion® lure (FIG. 10).

Lure longevity and release rate were evaluated using lures loaded with the binary, and trinary blends and exposed in the field for 6, 8, and 12 wk. GC analyses indicated that ~13 percent of the pheromone was evaporated and ~0.87-mg pheromone remained in the rubber septa lures exposed for 6 wk in the field from May to June in North Carolina, ~18 percent of the pheromone was evaporated and ~0.82-mg pheromone remained in the rubber septa lures exposed for 8 wk in the field from May to July in West Virginia, and ~24 percent of the pheromone was evaporated and ~0.76-mg pheromone still remained in the rubber septa lures exposed for 12 wk in the field from June to August in Virginia (Table 2). During these field tests, more than 26,000 males were caught in those binary and trinary blends-baited traps, whereas control traps caught no males.

On the basis of GC-EAD analyses of effluvial collections, gland extracts, synthetic isomers of 3,13- and 2,13-ODDA, and field trapping tests, we have demonstrated that Z,Z-3,13-ODDA was the main pheromone component of female DWB and it alone will reliably attract male DWB. However, we have surprisingly found that other components significantly increased attraction. When Z,Z,-3,13-ODD was combined with E, Z-2,13-ODDA in a 94:6 blend, captures were significantly greater than Z,Z-3,13-ODDA alone or Z,Z-3,13-ODDA in combination with Z,E-3,13-ODDA in 94:6 blend. Ultimately, though, the significantly greatest captures were recorded for traps baited with the trinary blend (Z,Z-3,13-ODDA E, Z-2,13-ODDA:Z,E-3,13-ODDA=88:6:6), compared to any other treatment across all locations (FIG. 2).

We found that two pheromone components, Z,Z-3,13-ODDA and E,Z-2,13-ODDA, were surprisingly absolutely essential for attraction of male DWB. When as little as 1% E,Z-2,13-ODDA was added to a 94:6 (Z,Z-3,13-ODDA:Z,E-3,13-ODDA) blend, captures surprisingly increased significantly in all locations (FIG. 4). We did not observe a similar response when Z,E-3,13-ODDA was added to a 94:6 (Z,Z-3,13-ODDA:E,Z2,13-ODDA) blend (FIG. 3).

Figure 2:
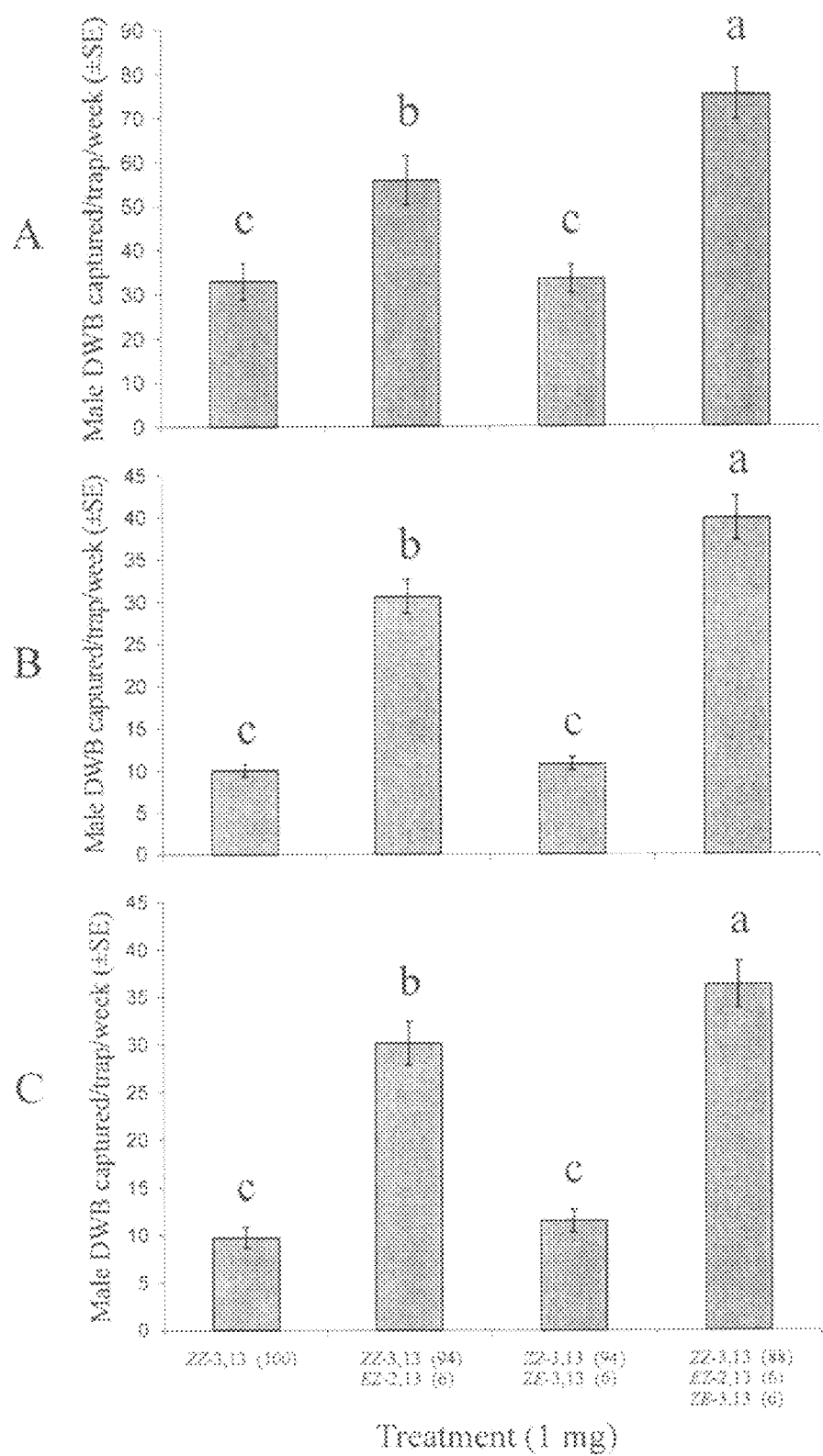
FIG. 2 shows results of DWB pheromone blend tests conducted as follows: (A) from May to July in North Carolina (NC), total number of male DWB trapped was 14,101, $N=70$, $df=3,276$, $F=63.32$; (B) from June to August in Virginia (VA), total number of male DWB trapped was 11,917, $N=130$, $df=3,516$, $F=112.12$; (C) from June to August in West Virginia (WV), total number of male DWB trapped was 10,506, $N=120$, $df=3,476$, $F=223.04$. Bars superscripted by different letters are statistically different (arcsin $\sqrt{p}$ transformed, where p is the original proportion, $p<0.05$).

However, without being bound by theory, we believe that Z,E-3,13-ODDA does synergize the response to the binary blend (Z,Z-3, 13-ODDA:E,Z-2,13-ODDA) based on the fact that significantly more captures were recorded in all locations with this trinary blend compared to the binary blend (FIG. 2). Furthermore, more male moths were captured with the trinary blend compared to the binary blend when compared with calling virgin female moths (FIG. 9). Ultimately, male DWB may not have been able to discriminate among treatments in our trial evaluating the addition of 0.5-10% Z,E-3,13-ODDA to the binary blend (Z,Z-3,13-ODDA:E,Z-2,13-ODDA) because the greatest distance between stimuli was approximately 20-25 m, whereas in our other field trial that compared the binary and trinary blends with our other treatments the distance between these two very attractive stimuli was as much as 120 m. As distance between attractive stimuli was reduced (as was the case in our evaluation of trinary blends of various ratios), it seems logical that male DWB would no longer discriminate among such similar and extremely attractive stimuli, thus accounting for our similar captures across treatments (FIG. 3).

We have documented the surprising pheromone antagonistic effect of E,Z-3,13-ODDA on Z,Z-3,13-ODDA. In field trials, surprising as little as 0.5% E,Z-3,13-ODDA added to our trinary blend significantly reduced trap captures in all locations (FIG. 5). The importance of this particular compound in terms of niche separation was clear. E,Z-3,13-ODDA elicited just as strong an electroantennogram response as Z,Z-3,13-ODDA from male DWB antennae (Table 1), but behaviorally this compound surprisingly served to inhibit (antagonize) DWB male response and movement toward what would otherwise would be a very attractive olfactory stimulus.

Figure 6:
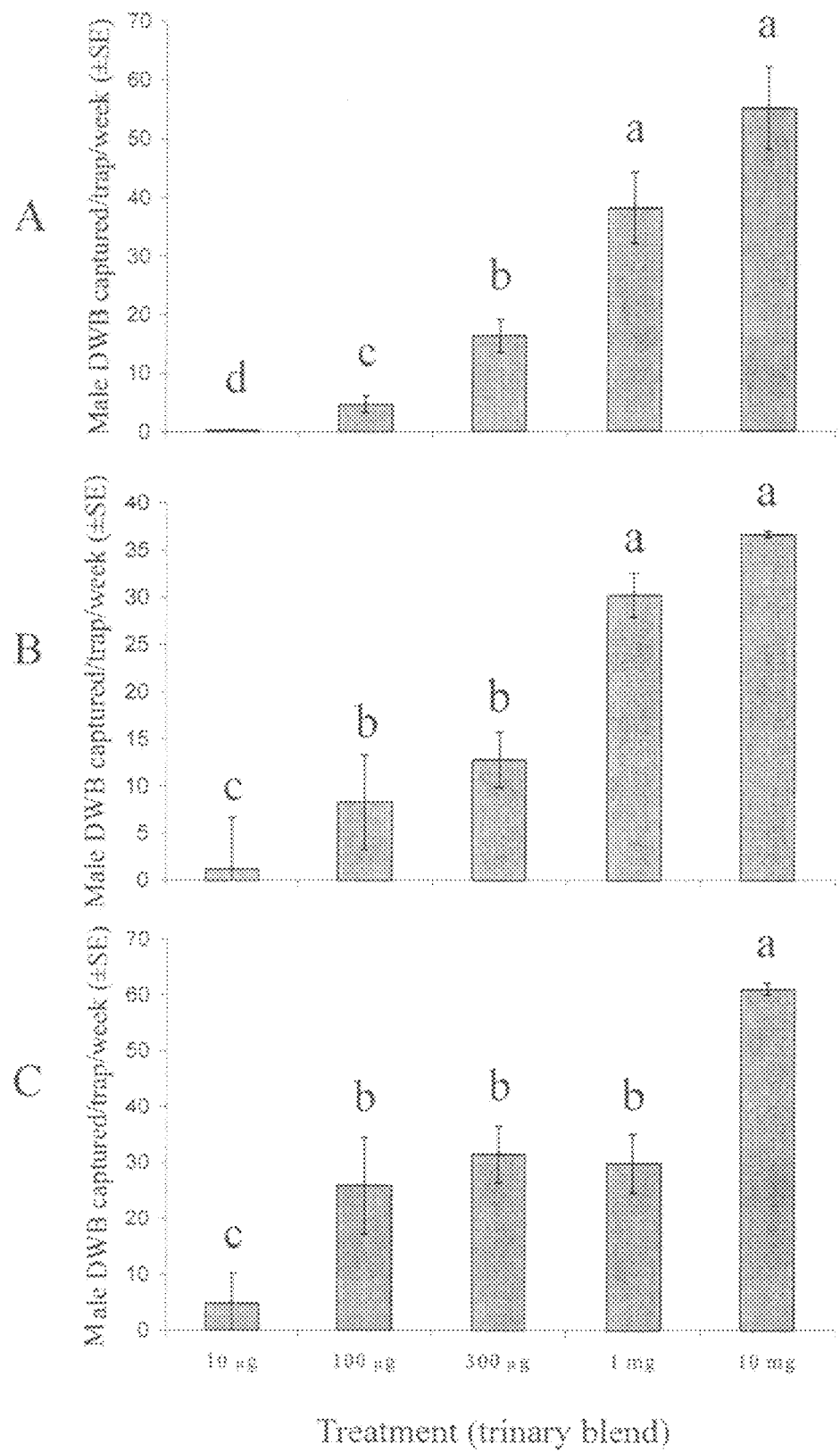
FIG. 6 shows results of DWB pheromone trinary blend dose tests conducted as follows: (A) from July to August in NC, total number of male DWB trapped was 2,394, $N=21$, $df=4,100$, $F=97.79$; (B) from July to August in VA, total number of male DWB trapped was 1,333, $N=15$, $df=4,70$, $F=35.61$; (C) from June to July in WV, total number of male DWB trapped was 2,296, $N=15$, $df=4,70$, $F=23.57$. Bars superscripted by different letters are statistically different ($p<0.05$).
Figure 7:
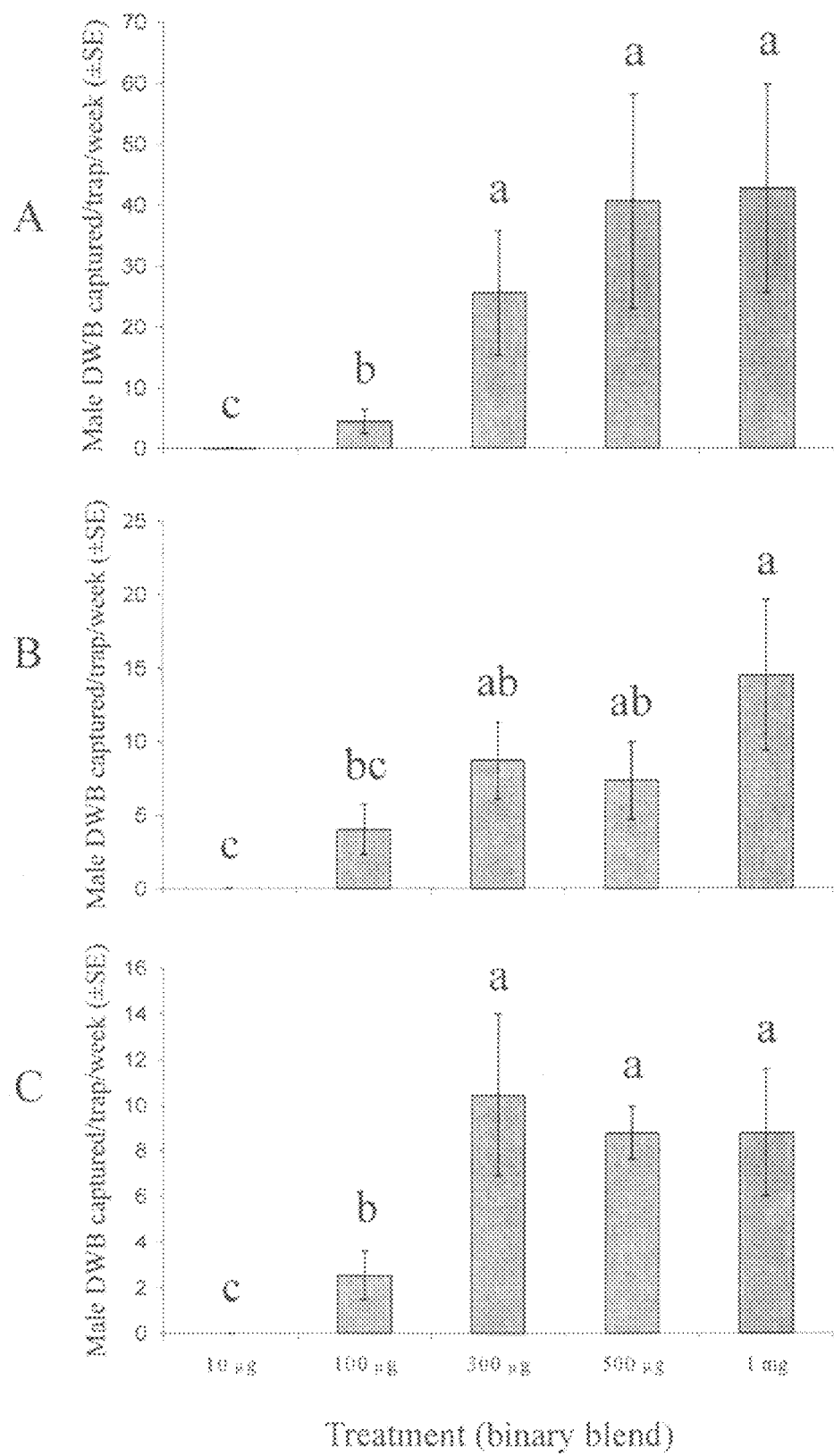
FIG. 7 shows results of DWB pheromone binary blend dose tests conducted as follows: (A) from September to October in NC, total number of male DWB trapped was 1,699, $N=15$, $df=4,70$, $F=16.72$; (B) from September to September in VA, total number of male DWB trapped was 207, $N=6$, $df=4,25$, $F=7.48$; (C) in September in WV, total number of male DWB trapped was 275, $N=9$, $df=4,40$, $F=14.97$. Bars superscripted by different letters are statistically different ($p<0.05$).

In terms of dose responses to the binary and trinary blends, significantly more male DWB were captured in traps baited with septa loaded with greater than 10-μg of material (FIGS. 6 and 7). With the trinary blend, the greatest numbers of males were captured with septa loaded with 10-mg, but this was not significantly different than captures with 1-mg (standard dose) septa in two locations (FIG. 6). For the binary blend, statistically equal numbers of male DWB were captured in traps baited with 300-μg, 500-μg, and 1-mg septa across all locations (FIG. 7). It seems likely that for monitoring purposes that the total amount of material could be reduced to approximately 500-μg and still maintain high trap captures. Furthermore, based on a survey of male captures within a highly infested orchard and at 50 and 100 m from the orchard in a wood lot, males reliably detected a trinary blend at distances of at least 50 m (FIG. 8).

Selectivity of pheromone lures is a critical factor in optimizing their effectiveness as monitoring tools. The percentage of dogwood borers captured with the trinary and binary blends was surprisingly greater than 97% across all locations, while the specificity of the Scenturion® lure for dogwood borers was much lower, ranging from 6.3-74.4% of total trap captures across locations (FIG. 10). Traps baited with commercial lures for dogwood borers commonly also capture large numbers of peachtree borers, since this species is a common pest of peach orchards and wild hosts that are often found in close proximity to apple orchards. In our studies, captures of peachtree borers were surprisingly very low, comprising between 0-1% across all locations (FIG. 10).

The results from release rate and lure longevity studies indicated that pheromone lures with 1-mg loading should have an effective lifetime over the whole flight season. This experiment was terminated only because of the seasonal decline in DWB populations rather than decline in the lure attractiveness. Chemical analyses of lures revealed that ~0.76-mg of pheromone remained in the 1-mg dose septa after 12 wk of field exposure (Table 2). These amounts of residual pheromones should still be sufficient to trigger and maintain the lure attraction for some time. Considering that release rate was affected by the temperature as well as wind speed, the dose of 1-mg lures did not need to be changed for the entire test season.

All of the references cited herein are incorporated by reference in their entirety. Also incorporated by reference in their entirety are the following references: Evenden, M. L., et al., J. Chem. Ecol., 25: 501-517 (1999); Evenden, M. L., et al., J. Econ. Entomol., 92:380-390 (1999); George, D., and P. Mallery, SPSS for Windows step by step: A simple guide and reference, 4th ed., 2002, Allyn & Bacon, Boston; Greenfield, M. D., Niche segregation of adult clearwing moths (*Lepidoptera*: Sesiidae) in Wisconsin, Ph.D. Thesis, University of Wisconsin, Madison, Wis., 138 pp. (1978); Karandinos, M. G., et al., J. Chem. Ecol., 3:57-64 (1977); Leskey, T. C., J. C. Bergh, J. F. Walgenbach, and A. Zhang, Improved attractiveness and specificity of pheromone-baited traps for male dogwood borer, *Synanthedon scitula* (Harris) (*Lepidoptera*: Sesiidae), Environ. Entomol. (submitted); McLaughlin, J. R., et al., Fl. Entomol., 60:27-29 (1977)); Nielsen, D. G., et al., Environ. Entomol., 4: 451-454 (1975); Pfeiffer, D. G., and J.

C. Killian, J. Entomol. Sci., 34: 210-218 (1999); Tumlinson, J. H., 1979, The chemistry of Sesiidae pheromones, pp. 1-10, In Pheromones of the Sesiidae (formerly Aegeriidae), US Department of Agriculture, Science and Education Administration, AAR-NE-6, Beltsville, Md. Also incorporated by reference in their entirety are the following U.S. Pat. Nos. 6,703,014; 6,479,046.

Thus, in view of the above, the present invention concerns (in part) the following:

A (synthetic or isolated or purified) composition comprising (or consisting essentially of or consisting of) Z,Z-3,13-octadecadienyl acetate, optionally E,Z-2,13-octadecadienyl acetate, optionally Z,E-3,13-octadecadienyl acetate, and optionally a carrier material or carrier (e.g., an agronomically or physiologically (pharmaceutically) acceptable carrier); said composition containing less than about 0.3% (or less than about 0.25% or less than 0.2% or less than 0.15% or less than about 0.1% or less than about 0.05% or about 0%) E,Z-3,13-octadecadienyl acetate based on the molar amount of said Z,Z-3,13-octadecadienyl acetate in said composition.

The above composition, wherein said composition comprises (or consists essentially of or consists of) Z,Z-3,13-octadecadienyl acetate, E,Z-2,13-octadecadienyl acetate, and Z,E-3,13-octadecadienyl acetate, and optionally a carrier material or carrier (e.g., an agronomically or physiologically (pharmaceutically) acceptable carrier).

The above composition, wherein said composition comprises (or consists essentially of or consists of) Z,Z-3,13-octadecadienyl acetate:E,Z-2,13-octadecadienyl acetate:Z,E-3,13-octadecadienyl acetate in a molar ratio of about 80:about 10:about 10 to about 99:about 0.5:about 0.5. The above composition, wherein said composition comprises (or consists essentially of or consists of) Z,Z-3,13-octadecadienyl acetate:E,Z-2,13-octadecadienyl acetate:Z,E-3,13-octadecadienyl acetate in a molar ratio of about 88:about 6:about 6.

The above composition, wherein said composition comprises (or consists essentially of or consists of) Z,Z-3,13-octadecadienyl acetate, E,Z-2,13-octadecadienyl acetate, and optionally a carrier material or carrier (e.g., an agronomically or physiologically (pharmaceutically) acceptable carrier); said composition containing less than about 0.3% (or less than about 0.25% or less than 0.2% or less than 0.15% or less than about 0.1% or less than about 0.05% or about 0%) Z,E-3,13-octadecadienyl acetate based on the molar amount of said Z,Z-3,13-octadecadienyl acetate in said composition.

The above composition, wherein said composition comprises (or consists essentially of or consists of) Z,Z-3,13-octadecadienyl acetate:E,Z-2,13-octadecadienyl acetate in a molar ratio of about 99.5:about 0.5 to about 90:about 10. The above composition, wherein said composition comprises (or consists essentially of or consists of) Z,Z-3,13-octadecadienyl acetate:E,Z-2,13-octadecadienyl acetate in a molar ratio of about 94:about 6.

The above composition, wherein said composition comprises (or consists essentially of or consists of) Z,Z-3,13-octadecadienyl acetate and optionally a carrier material or carrier (e.g., an agronomically or physiologically (pharmaceutically) acceptable carrier); said composition containing less than about 0.3% (or less than about 0.25% or less than 0.2% or less than 0.15% or less than about 0.1% or less than about 0.05% or about 0%) E,Z-2,13-octadecadienyl acetate and less than about 0.3% (or less than about 0.25% or less than 0.2% or less than 0.15% or less than about 0.1% or about 0.05% or about 0%) E Z-3,13-octadecadienyl acetate based on the molar amount of said Z,Z-3,13-octadecadienyl acetate in said composition.

A method for attracting male *Synanthedon scitula* to an object or area (or locus), comprising (or consisting essentially of or consisting of) treating said object or area (or locus) with a male *Synanthedon scitula* attracting composition comprising (or consisting essentially of or consisting of) a male *Synanthedon scitula* attracting effective amount of Z,Z-3,13-octadecadienyl acetate, optionally E,Z-2,13-octadecadienyl acetate, optionally Z,E-3,13-octadecadienyl acetate, and optionally a carrier material or carrier (e.g., an agronomically or physiologically (pharmaceutically) acceptable carrier); said composition containing less than about 0.3% (or less than about 0.25% or less than 0.2% or less than 0.15% or less than about 0.1% or less than about 0.05% or about 0%) E,Z-3,13-octadecadienyl acetate based on the molar amount of said Z,Z-3,13-octadecadienyl acetate in said composition.

The above method, wherein said composition comprises (or consists essentially of or consists of) Z,Z-3,13-octadecadienyl acetate, E,Z-2,13-octadecadienyl acetate, and Z,E-3,13-octadecadienyl acetate, and optionally a carrier material or carrier (e.g., an agronomically or physiologically (pharmaceutically) acceptable carrier).

The above method, wherein said composition comprises (or consists essentially of or consists of) Z,Z-3,13-octadecadienyl acetate, E,Z-2,13-octadecadienyl acetate, and optionally a carrier material or carrier (e.g., an agronomically or physiologically (pharmaceutically) acceptable carrier); said composition containing less than about 0.3% (or less than about 0.25% or less than 0.2% or less than 0.15% or less than about 0.1% or less than about 0.05% or about 0%) of Z,E-3,13-octadecadienyl acetate based on the molar amount of said Z,Z-3,13-octadecadienyl acetate in said composition.

The above method, wherein said composition comprises or consists essentially of or consists of) Z,Z-3,13-octadecadienyl acetate and optionally a carrier material or carrier (e.g. an agronomically or physiologically (pharmaceutically) acceptable carrier); said composition containing less than about 0.3% (or less than about 0.25% or less than 0.2% or less than 0.15% or less than about 0.1% or less than about 0.05% or about 0%) E,Z-2,13-octadecadienyl acetate and less than about 0.3% (or less than about 0.25% or less than 0.2% or less than 0.15% or less than about 0.1% or less than about 0.05% or about 0%) Z,E-3,13-octadecadienyl acetate based on the molar amount of said Z,Z-3,13-octadecadienyl acetate in said composition.

The above method, wherein >70% (or >75% or >80% or >85% or >90% or >95% or >96% or >97% or >98%) of the sesiids attracted are *Synanthedon scitula*.

A (synthetic or isolated or purified) composition, comprising (or consisting essentially of or consisting of) E,Z-3,13-octadecadienyl acetate, and optionally a carrier material or carrier (e.g., an agronomically or physiologically or pharmaceutically acceptable carrier).

The above composition, said composition containing about 0-about 70% Z,Z-3,13-octadecadienyl acetate, about 0-about 10% E,Z-2,13-octadecadienyl acetate, and about 0-about 10% Z,E-3,13-octadecadienyl acetate based on the molar amount of said E, Z-3,13-octadecadienyl acetate in said composition.

The above composition, said composition containing about 0% E, Z-2,13-octadecadienyl acetate and about 0% Z,E-3,13-octadecadienyl acetate based on the molar amount of said E,Z-3,13-octadecadienyl acetate in said composition.

A (synthetic or isolated or purified) composition for inhibiting male *Synanthedon scitula* attraction to female *Synanthedon scitula*, comprising (or consisting essentially of or consisting of) ingredients E,Z-3,13-octadecadienyl acetate and Z,Z-3,13-octadecadienyl acetate, and optionally a carrier material or carrier; wherein said ingredients in said composition that inhibit male *Synanthedon scitula* attraction to female *Synanthedon scitula* consist of about 75-100% by weight E,Z-3,13-octadecadienyl acetate and about 0-25% by weight Z,Z-3,13-octadecadienyl acetate.

The above composition, said composition containing about 0% E,Z-2,13-octadecadienyl acetate, about 0% Z,E-3,13-octadecadienyl acetate, and about 0% E,E-3,13-octadecadienyl acetate.

The above composition, wherein said ingredients in said composition that inhibit male *Synanthedon scitula* attraction to female *Synanthedon scitula* consist of about 80-100% by weight E,Z-3,13-octadecadienyl acetate and about 0-20% by weight Z,Z-3,13-octadecadienyl acetate. The above composition, wherein said ingredients in said composition that inhibit male. *Synanthedon scitula* attraction to female *Synanthedon scitula* consist of about 85-100% by weight E,Z-3,13-octadecadienyl acetate and about 0-15% by weight Z,Z-3,13-octadecadienyl acetate. The above composition, wherein said ingredients in said composition that inhibit male *Synanthedon scitula* attraction to female *Synanthedon scitula* consist of about 90-100% by weight E,Z-3,13-octadecadienyl acetate and about 0-10% by weight Z,Z-3,13-octadecadienyl acetate. The above composition, wherein said ingredients in said composition that inhibit male *Synanthedon scitula* attraction to female *Synanthedon scitula* consist of about 95-100% by weight E,Z-3,13-octadecadienyl acetate and about 0-5% by weight Z,Z-3,13-octadecadienyl acetate. The above composition, said composition consisting essentially of about 75-100% by weight E,Z-3,13-octadecadienyl acetate and about 0-25% by weight Z,Z-3,13-octadecadienyl acetate, and optionally a carrier material or carrier. The above composition, said composition consisting of about 75-100% by weight E,Z-3,13-octadecadienyl acetate and about 0-25% by weight Z,Z-3,13-octadecadienyl acetate, and optionally a carrier material or carrier.

A method for inhibiting male *Synanthedon scitula* attraction to female *Synanthedon scitula*, comprising (or consisting essentially of or consisting of) exposing a *Synanthedon scitula* population to a composition comprising (or consisting essentially of or consisting of) E,Z-3,13-octadecadienyl acetate in a quantity sufficient to inhibit male *Synanthedon scitula* attraction to female *Synanthedon scitula*, and optionally a carrier material or carrier (e.g., an agronomically or physiologically (pharmaceutically) acceptable carrier). The above method, said composition does not contain Z,Z-3,13-octadecadienyl acetate. The above method, said composition does not contain E,Z-2,13-octadecadienyl acetate. The above method, said composition does not contain Z,E-3,13-octadecadienyl acetate.

The above method, said composition comprising (or consisting essentially of) at least 0.5% by weight E,Z-3,13-octadecadienyl acetate (or at least 0.5% based on the molar amount of the Z,Z-3,13-ODDA in the composition). The above method, said composition comprising (or consisting essentially of) at least 1% by weight E,Z-3,13-octadecadienyl acetate (or at least 1% based on the molar amount of the Z,Z-3,13-ODDA in the composition). The above method, said composition comprising (or consisting essentially of) at least 5% by weight E,Z-3,13-octadecadienyl acetate (or at least 5% based on the molar amount of the Z,Z-3,13-ODDA in the composition).

The above method, said composition comprising (or consisting essentially of or consisting of) ingredients E,Z-3,13-octadecadienyl acetate and Z,Z-3,13-octadecadienyl acetate, and optionally a carrier material or carrier; wherein said ingredients in said composition that inhibit male *Synanthedon scitula* attraction to female *Synanthedon scitula* consist of about 75-100% by weight E,Z-3,13-octadecadienyl acetate and about 0-25% by weight Z,Z-3,13-octadecadienyl acetate. The above method, wherein said ingredients in said composition that inhibit male *Synanthedon scitula* attraction to female *Synanthedon scitula* consist of about 80-100% by weight E,Z-3,13-octadecadienyl acetate and about 0-20% by weight Z,Z-3,13-octadecadienyl acetate. The above method, wherein said ingredients in said composition that inhibit male *Synanthedon scitula* attraction to female *Synanthedon scitula* consist of about 85-100% by weight E,Z-3,13-octadecadienyl acetate and about 0-15% by weight Z,Z-3,13-octadecadienyl acetate. The above method, wherein said ingredients in said composition that inhibit male *Synanthedon scitula* attraction to female *Synanthedon scitula* consist of about 90-100% by weight E,Z-3,13-octadecadienyl acetate and about 0-10% by weight Z,Z-3,13-octadecadienyl acetate. The above method, wherein said ingredients in said composition that inhibit male *Synanthedon scitula* attraction to female *Synanthedon scitula* consist of about 95-100% by weight E,Z-3,13-octadecadienyl acetate and about 0-5% by weight Z,Z-3,13-octadecadienyl acetate. The above method, said composition consisting essentially of about 75-100% by weight E,Z-3,13-octadecadienyl acetate and about 0-25% by weight Z octadecadienyl acetate, and optionally a carrier material or carrier. The above method, said composition consisting of about 75-100% by weight E,Z-3,13-octadecadienyl acetate and about 0-25% by weight Z,Z-3,13-octadecadienyl acetate, and optionally a carrier material or carrier.

A method for mass trapping male *Synanthedon scitula*, comprising (or consisting essentially of or consisting of) exposing a *Synanthedon scitula* population to a composition comprising (or consisting essentially of or consisting of) Z,Z-3,13-octadecadienyl acetate, optionally E,Z-2,13-octadecadienyl acetate, and optionally Z,E-3,13-octadecadienyl acetate in a quantity sufficient to reduce the male *Synanthedon scitula* population available to impregnate female *Synanthedon scitula*, and optionally a carrier material or carrier.

A method for disrupting male *Synanthedon scitula* mating with female *Synanthedon scitula*, comprising (or consisting essentially of or consisting of) exposing a *Synanthedon scitula* population to a composition comprising (or consisting essentially of or consisting of) Z,Z-3,13-octadecadienyl acetate, optionally E,Z-2,13-octadecadienyl acetate, and optionally Z,E-3,13-octadecadienyl acetate in a quantity sufficient to disrupt male *Synanthedon scitula* mating with female *Synanthedon scitula*, and optionally a carrier material or carrier (e.g., an agronomically or physiologically (pharmaceutically) acceptable carrier); wherein said composition contains less than about 0.3% (or less than about 0.25% or less than 0.2% or less than 0.15% or less than about 0.1% or less than about 0.05% or about 0%) E,Z-3,13-octadecadienyl acetate based on the molar amount of said Z,Z-3,13-octadecadienyl acetate in said composition.

A method for attracting male *Synanthedon scitula* to an object or area or locus, comprising (or consisting essentially of, consisting of) exposing said male *Synanthedon scitula* to a trap charged with an attracting composition comprising (or consisting essentially of or consisting of) a male *Synanthedon scitula* attractant effective amount of Z,Z-3,13-octadecadienyl acetate, optionally E,Z-2,13-octadecadienyl acetate, optionally Z,E-3,13-octadecadienyl acetate, and optionally a carrier material or carrier; said composition containing less than about 0.3% (or less than about 0.25% or less than 0.2% or less than 0.15% or less than about 0.1% or less than about 0.05% or about 0%) E,Z-3,13-octadecadienyl acetate based on the molar amount of said Z,Z-3,13-octadecadienyl acetate in said composition.

The carrier or carrier material as used herein is defined as not including the body of an insect (e.g., male and/or female *Synanthedon scitula*).

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Retention Times of EAD-Active Compounds Obtained from Gland and Effluvial Extracts of Female DWB and Synthetic 3,13- and 2,13-Octadecadienyl Acetates.

| Compounds | Retention time (min) | | EAD activity in 10 ng of loading |
|---|---|---|---|
| | DB-WAXETR | DB-5 | (mV)[a] |
| From females: | | | |
| (Z, 2)-3,13-Octadecadienyl acetate | 14.48 | 13.82 | |
| (E, Z)-2,13-Octadecadienyl acetate | 14.75 | 13.93 | |
| Synthetic: | | | |
| (E,E)-3,13-Octadecadienyl acetate | 14.39 | 13.81 | 0.12 (±3.5% SD, n = 3) |
| (Z,E)-3,13-Octadecadienyl acetate | 14.42 | 13.80 | 0.25 (±1.0% SD, n = 3) |
| (E,Z)-3,13-Octadecadienyl acetate | 14.44 | 13.83 | 0.30 (±8.7% SD, n = 3) |
| (Z,Z)-3,13-Octadecadienyl acetate | 14.48 | 13.82 | 0.30 (±9.5% SD, n = 3) |
| (Z,E)-2,13-Octadecadienyl acetate | 14.46 | 13.84 | 0.030 (±0.10% SD, n = 3) |
| (Z,Z)-2,13-Octadecadienyl acetate | 14.53 | 13.86 | 0.029 (±0.79% SD, n = 3) |
| (E,E)-2,13-Octadecadienyl acetate | 14.68 | 13.90 | 0.012 (±0.21% SD, n = 3) |
| (E,Z)-2,13-Octadecadienyl acetate | 14.75 | 13.93 | 0.13 (±1.2% SD, n = 3) |

[a]Relative to E,Z-2,13-octadecadienyl acetate.

TABLE 2

Mean Amount of Pheromone Components Remaining in the Lures After Exposure Under Field Conditions.[a]

| Orchard | Blend | 6 wk[b] | 8 wk[c] | 12 wk[d] |
|---|---|---|---|---|
| 1 | Binary | 0.87 (±5.5% SD, n = 5) | | |
| 2 | Binary | | 0.79 (±7.9% SD, n = 5) | |
| 1 | Trinary | 0.86 (±9.4% SD, n = 5) | | |
| 2 | Trinary | | 0.84 (±6.2% SD, n = 5) | |
| 1 | Binary | | | 0.72 (±3.8% SD, n = 5) |
| 2 | Binary | | | 0.75 (±1.7% SD, n = 5) |
| 1 | Trinary | | | 0.81 (±2.6% SD, n = 5) |
| 2 | Trinary | | | 0.77 (±5.1% SD, n = 5) |

[a]Original loading was 1.0 mg/septum.
[b]Exposed from May to June in North Carolina.
[c]Exposed from May to July in North Carolina.
[d]Exposed from June to August in Virginia.

TABLE 3

Total number of males captured and mean no. males per trap per week in monitoring traps baited with the DWB complete pheromone blend sex pheromone and deployed in blocks treated with a behavioral antagonist blend or untreated in two commercial orchards in West Virginia

| Location | Block Treatment | Total No. Captured | Mean ± SE |
|---|---|---|---|
| Arden, WV | Untreated | 2578 | 53.70 ± 7.90* |
| | Antagonist Blend | 12 | 0.25 ± 0.11 |
| Inwood, WV | Untreated | 1085 | 19.04 ± 2.52* |
| | Antagonist Blend | 1 | 0.02 ± 0.02 |

*Indicates significantly more males captured per trap based on a Student's t-test (P < 0.05).

We claim:

1. A composition comprising Z,Z-3,13-octadecadienyl acetate, E,Z-2,13-octadecadienyl acetate, Z,E-3,13-octadecadienyl acetate, and a physiologically acceptable carrier material or carrier; wherein said composition comprises Z,Z-3,13-octadecadienyl acetate:E,Z-2,13-octadecadienyl acetate:Z,E-3,13-octadecadienyl acetate in a molar ratio of about 80:about 10:about 10 to about 99:about 0.5:about 0.5; said composition containing less than 0.3% or about 0.3% E,Z-3,13-octadecadienyl acetate based on the molar amount of said Z, Z-3,13-octadecadienyl acetate in said composition.

2. The composition according to claim 1, wherein said composition contains less than 0.25% or about 0.25% E,Z-3, 13-octadecadienyl acetate based on the molar amount of said Z,Z-3,13-octadecadienyl acetate in said composition.

3. The composition according to claim 1, wherein said composition comprises Z,Z-3,13-octadecadienyl acetate:E, Z-2,13-octadecadienyl acetate:E-3,13-octadecadienyl acetate in a molar ratio of 80:10:10 to 99:0.5:0.5.

4. The composition according to claim 1, wherein said composition comprises Z,Z-3,13-octadecadienyl acetate:E, Z-2,13-octadecadienyl acetate:Z,E-3,13-octadecadienyl acetate in a molar ratio of about 88:about 6:about 6, and a physiologically acceptable carrier material or carrier.

5. The composition according to claim 1, wherein said composition comprises Z,Z-3,13-octadecadienyl acetate:E, Z-2,13-octadecadienyl acetate:Z,E-3,13-octadecadienyl acetate in a molar ratio of 88:6:6, and a physiologically acceptable carrier material or carrier.

6. The composition according to claim 1, wherein said composition contains less than 0.25% E,Z-3,13-octadecadienyl acetate based on the molar amount of said Z,Z-3,13-octadecadienyl acetate in said composition.

7. The composition according to claim 1, wherein said composition contains less than 0.2% E,Z-3,13-octadecadienyl acetate based on the molar amount of said Z,Z-3,13-octadecadienyl acetate in said composition.

8. The composition according to claim 1, wherein said composition contains less than 0.15% E,Z-3,13-octadecadienyl acetate based on the molar amount of said Z, Z-3,13-octadecadienyl acetate in said composition.

9. The composition according to claim 1, wherein said composition contains less than 0.1% E,Z-3,13-octadecadienyl acetate based on the molar amount of said Z,Z-3,13-octadecadienyl acetate in said composition.

10. The composition according to claim 1, wherein said composition contains less than 0.05% E,Z-3,13-octadecadienyl acetate based on the molar amount of said Z,Z-3,13-octadecadienyl acetate in said composition.

11. The composition according to claim 1, wherein said composition consists essentially of Z,Z-3,13-octadecadienyl acetate, E,Z-2,13-octadecadienyl acetate, Z,E-3,13-octadecadienyl acetate, and a physiologically acceptable carrier material or carrier; said composition containing less than 0.3% E,Z-3,13-octadecadienyl acetate based on the molar amount of said Z,Z-3,13-octadecadienyl acetate in said composition.

12. A method for attracting male *Synanthedon scitula* to an object or area, comprising treating said object or area with a male *Synanthedon scitula* attracting composition comprising a male *Synanthedon scitula* attracting effective amount of Z,Z-3,13-octadecadienyl acetate, E,Z-2,13-octadecadienyl acetate, Z,E-3,13-octadecadienyl acetate, and a physiologically acceptable carrier material or carrier; wherein said composition comprises Z,Z-3,13-octadecadienyl acetate:E,Z-2,13-octadecadienyl acetate:Z,E-3,13-octadecadienyl acetate in a molar ratio of about 80:about 10:about 10 to about 99:about 0.5:about 0.5; said composition containing less than 0.3% or about 0.3% E,Z-3,13-octadecadienyl acetate based on the molar amount of said Z,Z-3,13-octadecadienyl acetate in said composition.

13. The method according to claim 12, wherein said composition consists essentially of Z,Z-3,13-octadecadienyl acetate, E,Z-2,13-octadecadienyl acetate, and Z,E-3,13-octadecadienyl acetate, and a physiologically acceptable carrier material or carrier; said composition containing less than 0.3% E,Z-3,13-octadecadienyl acetate based on the molar amount of said Z,Z-3,13-octadecadienyl acetate in said composition.

14. The method according to claim 12, wherein said composition comprises Z,Z-3,13-octadecadienyl acetate:E,Z-2,13-octadecadienyl acetate:Z,E-3,13-octadecadienyl acetate in a molar ratio of 80:10:10 to 99:0.5:0.5.

15. The method according to claim 12, wherein said composition comprises Z,Z-3,13-octadecadienyl acetate:E,Z-2,13-octadecadienyl acetate:Z,E-3,13-octadecadienyl acetate in a molar ratio of about 88:about 6:about 6, and a physiologically acceptable carrier material or carrier.

16. The method according to claim 12, wherein said composition comprises Z,Z-3,13-octadecadienyl acetate:E,Z-2,13-octadecadienyl acetate:Z,E-3,13-octadecadienyl acetate in a molar ratio of 88:6:6, and a physiologically acceptable carrier material or carrier.

17. The method according to claim 12, wherein said composition contains less than 0.25% of E,Z-3,13-octadecadienyl acetate based on the molar amount of said Z,Z-3,13-octadecadienyl acetate in said composition.

18. The method according to claim 12, wherein said composition contains less than 0.2% of E,Z-3,13-octadecadienyl acetate based on the molar amount of said Z,Z-3,13-octadecadienyl acetate in said composition.

19. The method according to claim 12, wherein said composition contains less than 0.15% of E,Z-3,13-octadecadienyl acetate based on the molar amount of said Z,Z-3,13-octadecadienyl acetate in said composition.

20. The method according to claim 12, wherein said composition contains less than 0.1% of E,Z-3,13-octadecadienyl acetate based on the molar amount of said Z,Z-3,13-octadecadienyl acetate in said composition.

21. The method according to claim 12, wherein said composition contains less than 0.05% of E,Z-3,13-octadecadienyl acetate based on the molar amount of said Z,Z-3,13-octadecadienyl acetate in said composition.

* * * * *